United States Patent
Wakai et al.

(10) Patent No.: US 10,888,290 B2
(45) Date of Patent: *Jan. 12, 2021

(54) MEDICAL-IMAGE PROCESSING APPARATUS AND MEDICAL-IMAGE DIAGNOSTIC APPARATUS

(71) Applicant: CANON MEDICAL SYSTEMS CORPORATION, Otawara (JP)

(72) Inventors: Satoshi Wakai, Nasushiobara (JP); Takuya Sakaguchi, Utsunomiya (JP); Akihito Takahashi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,771

(22) Filed: Sep. 18, 2017

(65) Prior Publication Data

US 2018/0020998 A1  Jan. 25, 2018

Related U.S. Application Data

(62) Division of application No. 14/617,082, filed on Feb. 9, 2015.

(30) Foreign Application Priority Data

Feb. 10, 2014  (JP) .................................. 2014-023740

(51) Int. Cl.
*A61B 6/00*  (2006.01)
(52) U.S. Cl.
CPC ............ *A61B 6/466* (2013.01); *A61B 6/5247* (2013.01); *G06T 2207/10004* (2013.01); *G06T 2207/10072* (2013.01); *G06T 2207/30101* (2013.01)

(58) Field of Classification Search
None
See application file for complete search history.

(56) References Cited

U.S. PATENT DOCUMENTS

| 8,157,742 B2 | 4/2012 | Taylor |
| 2009/0010519 A1* | 1/2009 | Wakai ................... G06F 19/321 382/131 |

(Continued)

FOREIGN PATENT DOCUMENTS

| JP | 2003-525067 A | 8/2003 |
| JP | 2004-528920 A | 9/2004 |

(Continued)

OTHER PUBLICATIONS

Office Action dated Nov. 13, 2018 in Japanese Patent Application No. 2015-024491.

*Primary Examiner* — Yanna Wu
(74) *Attorney, Agent, or Firm* — Oblon, McClelland, Maier & Neustadt, L.L.P.

(57) ABSTRACT

A medical-image processing apparatus and a medical-image diagnostic apparatus according to an embodiment include an acquisition unit, a generation unit, an identification unit, and a display control unit. The acquisition unit acquires a medical image containing a blood vessel collected by the medical-image diagnostic apparatus. The generation unit generates an anatomical structure model based on the medical image acquired by the acquisition unit. The identification unit identifies a position, on the medical image, of an index relating to blood flow analyzed through fluid analysis using the anatomical structure model. The display control unit displays the position of the index on the medical image, and also displays the index associated with the position of the index on the medical image.

29 Claims, 15 Drawing Sheets

(56) References Cited

U.S. PATENT DOCUMENTS

| | | | |
|---|---|---|---|
| 2012/0053918 A1 | 3/2012 | Taylor | |
| 2012/0101368 A1* | 4/2012 | Masumoto | A61B 6/503 600/420 |
| 2013/0004039 A1 | 1/2013 | Masumoto | |
| 2013/0116550 A1 | 5/2013 | Ishii | |
| 2013/0287728 A1* | 10/2013 | Pecora | A61K 35/28 424/85.1 |

FOREIGN PATENT DOCUMENTS

| | | |
|---|---|---|
| JP | 2010-526556 A | 8/2010 |
| JP | 2011-156321 A | 8/2011 |
| JP | 2012-90669 A | 5/2012 |
| WO | WO 00/53081 A1 | 9/2000 |
| WO | WO 02/094339 A2 | 11/2002 |
| WO | WO 2008/062358 A1 | 5/2008 |
| WO | WO 2012/021307 A2 | 2/2012 |
| WO | WO 2013/031741 A1 | 3/2013 |

\* cited by examiner

FIG.3
<CT IMAGE>
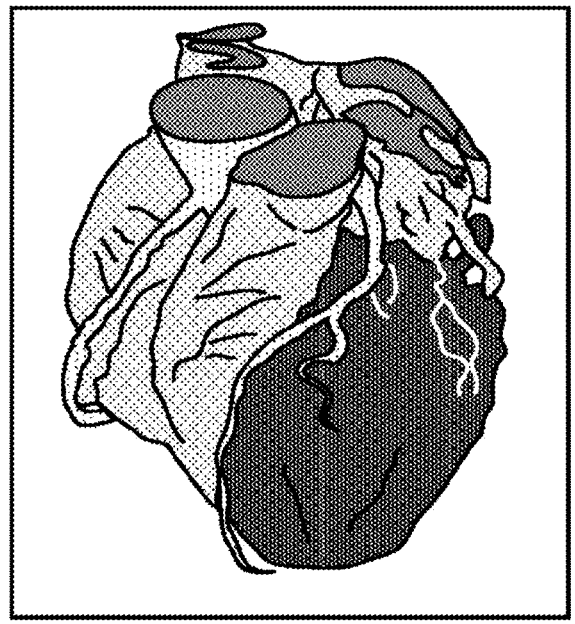
<3D CORONARY MODEL>
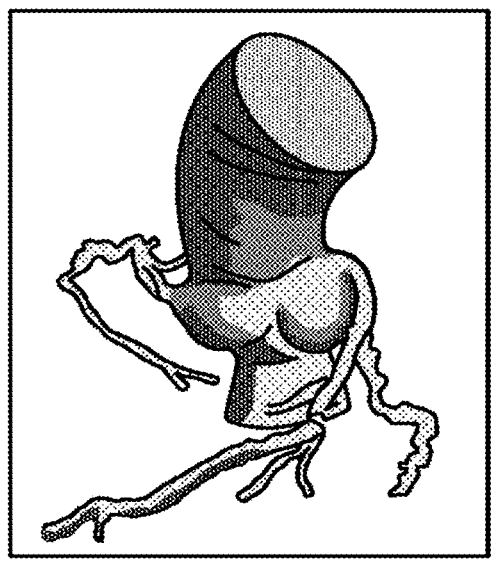

MEDICAL-IMAGE PROCESSING APPARATUS AND MEDICAL-IMAGE DIAGNOSTIC APPARATUS

CROSS-REFERENCE TO RELATED APPLICATIONS

This application is a divisional Application of U.S. application Ser. No. 14/617,082, filed Feb. 9, 2015, which is based upon and claims the benefit of priority from Japanese Patent Application No. 2014-023740, filed on Feb. 10, 2014. The entire contents of the above-identified applications are incorporated herein by reference.

FIELD

Embodiments described herein relate generally to a medical-image processing apparatus and a medical-image diagnostic apparatus.

BACKGROUND

In recent years, coronary stenosis lesions have been diagnosed from both aspects of "anatomical evaluation" of morphologically evaluating the presence or absence of stenosis and the degree of the stenosis, for example, and "physiological evaluation" of objectively evaluating the presence or absence of myocardial ischemia and the degree of the myocardial ischemia, for example. As physiological indices used for the "physiological evaluation", fractional flow reserve (FFR) and coronary flow reserve (CFR), for example, are drawing attention. For example, the FFR is an index that indicates the degree of myocardial ischemia caused by stenosis of a coronary artery, and is represented by the ratio of maximum coronary blood flow in the presence of stenosis to maximum coronary blood flow in the absence of stenosis. For example, the CFR is an index that indicates the ability to increase the coronary blood flow in response to the increasing demands of oxygen in a cardiac muscle, and is represented by the ratio of coronary blood flow during peak reactive hyperemia to coronary blood flow at rest.

These physiological indices have been conventionally calculated by certain measuring devices. However, in these years, an analysis technique is known in which the above-described physiological indices are calculated based on analysis using image data containing blood vessels. For example, CT-FFR is known in which an anatomical structure model (three-dimensional polygon model) of coronary arteries is generated from a CT image containing coronary arteries collected by an X-ray CT apparatus, and fluid analysis (computational fluid dynamics (CFD)) processing is applied to the generated three-dimensional polygon, whereby pressure distribution, blood velocity distribution, and FFR values, for example, in the coronary arteries are simulated to display these results on the three-dimensional polygon model. However, in the above-described conventional techniques, it may be difficult to compare the results of the fluid analysis with medical images.

BRIEF DESCRIPTION OF THE DRAWINGS

FIG. 3 includes diagrams illustrating one example of generation of a 3D coronary model by a 3D-coronary-model generating unit according to the first embodiment.

DETAILED DESCRIPTION

According to embodiment, a medical-image processing apparatus comprising an acquisition unit, a generation unit, an identification unit and a display control unit. The acquisition unit that acquires a medical image containing a blood vessel collected by a medical-image diagnostic apparatus. The generation unit that generates an anatomical structure model based on the medical image acquired by the acquisition unit. The identification unit that identifies a position, on the medical image, of an index relating to blood flow that is analyzed through fluid analysis using the anatomical structure model. The display control unit that displays the position of the index on the medical image, and also display the index associated with the position of the index on the medical image.

A medical-image processing apparatus and a medical-image diagnostic apparatus according to embodiments will now be described with reference to the drawings. In the embodiments below, embodiments of this medical-image processing apparatus 100 will be described.

Figure 1:
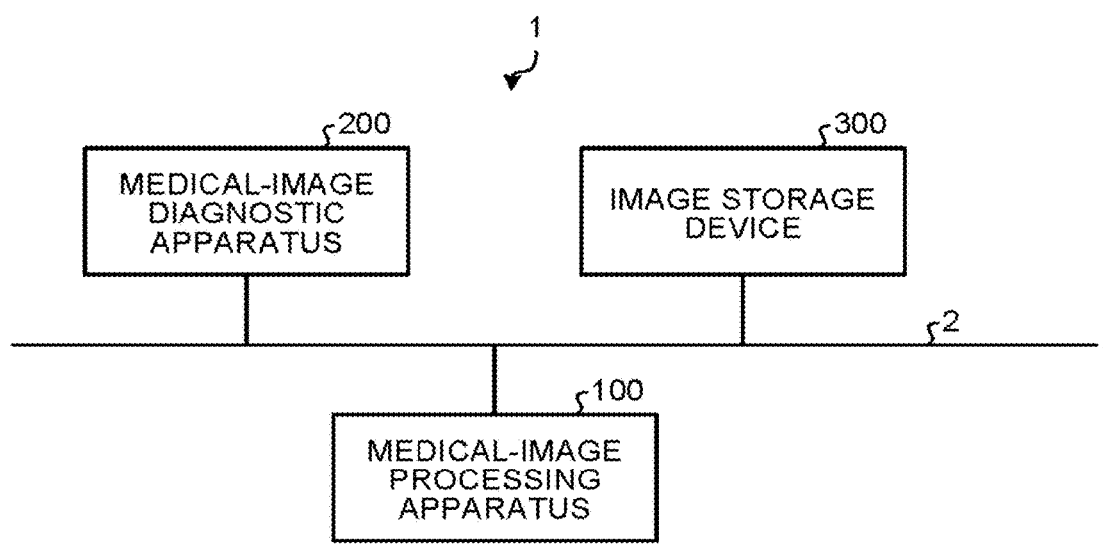
FIG. 1 is a diagram for explaining a configuration example of a system including a medical-image processing apparatus according to a first embodiment.

FIG. 1 is a diagram for explaining a configuration example of a system 1 including the medical-image processing apparatus 100 according to a first embodiment. As depicted in FIG. 1, the medical-image processing apparatus 100 according to the first embodiment is connected with a medical-image diagnostic apparatus 200 and an image storage device 300 via a network 2 such as an in-house local area network (LAN) installed in a hospital, for example. The respective apparatus and device herein can directly or indirectly communicate with each other. For example, when a picture archiving and communication system (PACS) is integrated in the system 1, the respective apparatus and device transmit and receive medical images, for example, between each other according to the Digital Imaging and Communications in Medicine (DICOM) standard.

The medical-image diagnostic apparatus 200 is an X-ray diagnostic apparatus, an X-ray computed tomography (CT) apparatus, a magnetic resonance imaging (MRI) apparatus, an ultrasonic diagnostic apparatus, a single photon emission computed tomography (SPECT) apparatus, a positron emission computed tomography (PET) apparatus, a SPECT-CT apparatus in which the SPECT apparatus and the X-ray CT apparatus are integrated, a PET-CT apparatus in which the PET apparatus and the X-ray CT apparatus are integrated, or a group of these apparatus, for example. The medical-image diagnostic apparatus 200 according to the first embodiment can generate three-dimensional medical-image data (volume data).

Specifically, the medical-image diagnostic apparatus 200 according to the first embodiment generates volume data by imaging a subject. For example, the medical-image diagnostic apparatus 200 collects data such as projection data and an MR signal by imaging a subject, and reconstructs medical-image data in a plurality of axial planes along the body axis of the subject from the collected data, thereby generating volume data. For example, the medical-image diagnostic apparatus 200 reconstructs medical-image data in 500 axial planes. This group of medical-image data in 500 axial planes constitutes the volume data. The projection data and the MR signal, for example, themselves of the subject imaged by the medical-image diagnostic apparatus 200 may be used as the volume data.

The medical-image diagnostic apparatus 200 according to the first embodiment transmits the generated volume data to the image storage device 300. When transmitting the volume data to the image storage device 300, the medical-image diagnostic apparatus 200 transmits as supplementary information, for example, a patient ID for identifying a subject, a test ID for identifying a test, an apparatus ID for identifying the medical-image diagnostic apparatus 200, a series ID for identifying one shot of imaging by the medical-image diagnostic apparatus 200.

The image storage device 300 is a database for storing medical images. Specifically, the image storage device 300 according to the first embodiment stores the volume data transmitted from the medical-image diagnostic apparatus 200 in a storage unit to store therein the volume data. In the first embodiment, the volume data stored in the image storage device 300 is stored in association with the patient ID, the test ID, the apparatus ID, and the series ID, for example. Accordingly, the medical-image processing apparatus 100 performs a search using the patient ID, the test ID, the apparatus ID, and the series ID, for example, to acquire necessary volume data from the image storage device 300.

The medical-image processing apparatus 100 is an image processing apparatus that performs image processing on medical images, and examples thereof include a workstation, an image server or a viewer of the picture archiving and communication system (PACS), and various devices of an electronic health record system. The medical-image processing apparatus 100 according to the first embodiment performs various processes on the volume data acquired from the medical-image diagnostic apparatus 200 or the image storage device 300, performs simulation of a physiological index for evaluating the presence or absence of myocardial ischemia or the degree of the myocardial ischemia, for example, to display a simulation result and a medical image. Herein, the medical-image processing apparatus 100 according to the present embodiment makes it possible to easily compare the simulation result of the physiological index based on the fluid analysis with the medical image.

As described above, in the conventional techniques, simulation of a physiological index based on the fluid analysis has been performed, and the simulation result is displayed on a three-dimensional polygon model. When the three-dimensional polygon model is compared with a medical image collected by the medical-image diagnostic apparatus, information such as pixel values and structural information of anatomical tissues is missing or reduced. Accordingly, only simultaneously displaying the simulation result and the three-dimensional polygon model is not sufficient for diagnostic performance, and thus comparison with the medical image may be required. For example, in a three-dimensional polygon model that is generated by rough modeling, there are occasions when stenosis is not recognized on the model and occasions when confirmation with the medical image is required. In view of this, the medical-image processing apparatus 100 according to the present embodiment makes it possible to easily compare the result based on the fluid analysis with the medical image by the configuration described in detail hereinafter.

Specifically, the medical-image processing apparatus 100 according to the present embodiment generates an anatomical structure model (e.g., three-dimensional polygon model) based on a medical image generated by the medical-image diagnostic apparatus 200, and performs fluid analysis processing on the generated anatomical structure model to acquire a simulation result of a physiological index (e.g., FFR or CFR). The medical-image processing apparatus 100 then aligns the acquired simulation result with the medical image to display a fusion image indicating the simulation result at the corresponding position in the medical image thus aligned.

Figure 2:
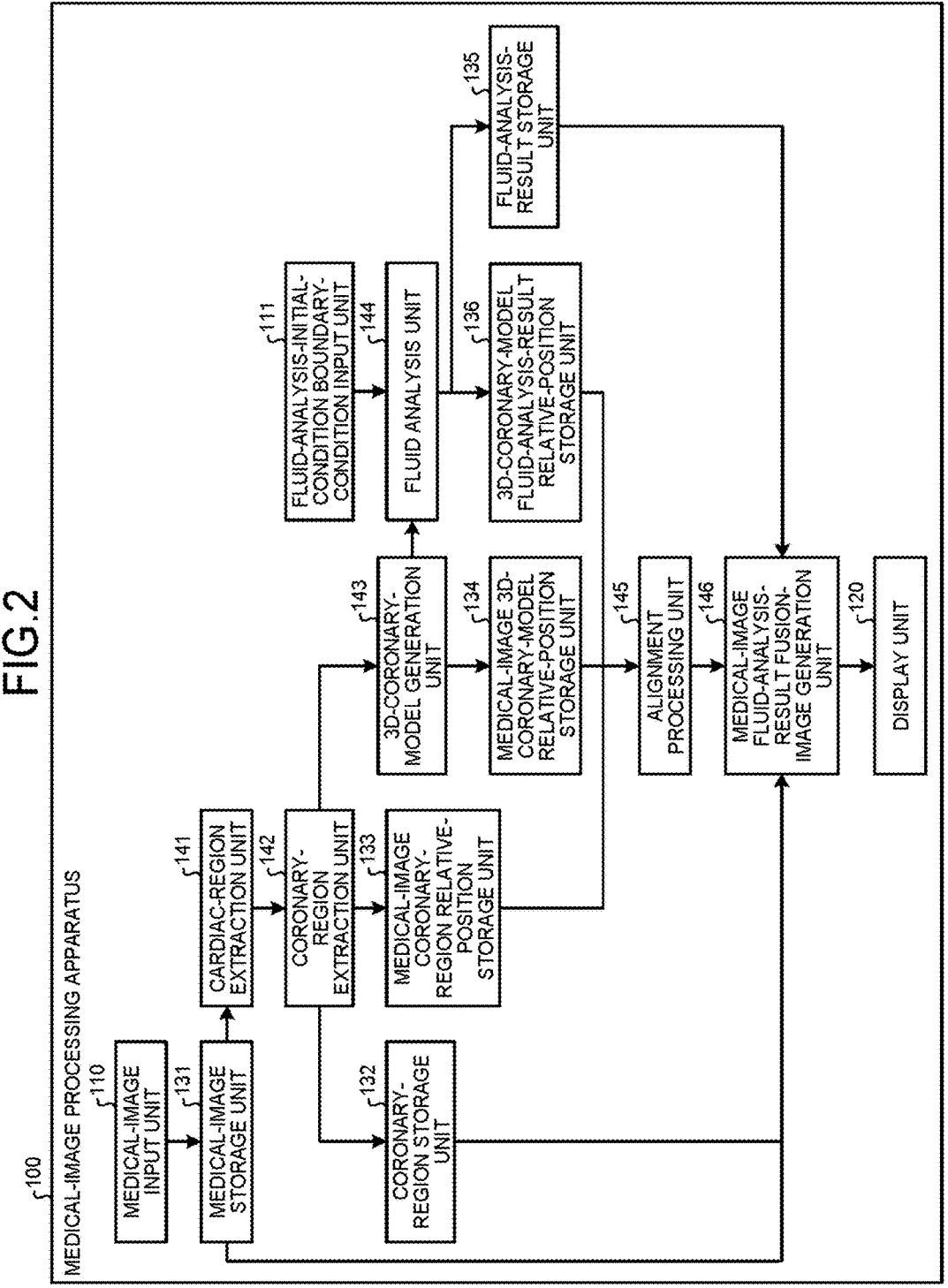
FIG. 2 is a diagram illustrating one example of configuration of the medical-image processing apparatus according to the first embodiment.

FIG. 2 is a diagram illustrating one example of configuration of the medical-image processing apparatus 100 according to the first embodiment. A medical-image input unit 110 acquires volume data of a medical image from the medical-image diagnostic apparatus 200 or the image storage device 300. Specifically, the medical-image input unit 110 acquires an image containing blood vessels collected by the medical-image diagnostic apparatus 200. The image containing blood vessels herein is an image of blood vessels such as coronary arteries that are imaged as targets, and includes a medical image collected in contrast imaging and a medical image collected in non-contrast imaging.

For example, the medical-image input unit 110 receives operation performed by an operator, and acquires volume data of a CT image in a cardiac region containing coronary arteries collected by an X-ray CT apparatus as the medical-image diagnostic apparatus 200. The medical-image input unit 110 then stores the acquired volume data in a medical-image storage unit 131. Herein, the medical-image input unit 110 can not only acquire the volume data of a medical image via the network 2 but also acquire the volume data via a portable storage medium.

The medical-image storage unit 131 stores therein the medical image acquired by the medical-image input unit 110. For example, the medical-image storage unit 131 stores therein the volume data of a CT image in a cardiac region containing coronary arteries acquired by the medical-image input unit 110.

A cardiac-region extraction unit 141 reads volume data of a medical image from the medical-image storage unit 131, and extracts the cardiac region from the volume data thus read. Herein, extraction of the cardiac region by the cardiac-region extraction unit 141 can be performed by existing known techniques. For example, the cardiac-region extraction unit 141 uses pattern matching using a human body atlas or a region expansion method based on pixel values (voxel values) of the volume data, for examples, to extract positions of voxels corresponding to the cardiac region in the volume data.

A coronary-region extraction unit 142 then extracts a coronary region contained in the cardiac region extracted by the cardiac-region extraction unit 141. Herein, extraction of the coronary region by the coronary-region extraction unit 142 can also be performed by existing known techniques. For example, the coronary-region extraction unit 142 uses the region expansion method, for example, to extract positions of voxels corresponding to the coronary region from the voxels corresponding to the cardiac region. In one example, the coronary-region extraction unit 142 extracts positions of voxels corresponding to the coronary region on the basis of CT values of voxels that vary depending on contrast agents in the CT image for the cardiac region.

The coronary-region extraction unit 142 then stores image data of the coronary region thus extracted in a coronary-region storage unit 132. The coronary-region extraction unit 142 also stores information on the position of the coronary region extracted in the medical image in a medical-image coronary-region relative-position storage unit 133. In other words, based on the information on the positions of the voxels corresponding to the cardiac region in the medical image extracted by the cardiac-region extraction unit 141, the coronary-region extraction unit 142 extracts positions of voxels, in the volume data of the medical image, that correspond to the coronary region extracted from the cardiac region, and stores information on the extracted positions in the medical-image coronary-region relative-position storage unit 133.

The coronary-region storage unit 132 stores therein image data of the coronary region extracted by the coronary-region extraction unit 142. The medical-image coronary-region relative-position storage unit 133 stores therein information on the positions of voxels, in the volume data of the medical image, that correspond to the coronary region extracted by the coronary-region extraction unit 142.

A 3D-coronary-model generation unit 143 generates a 3D coronary model in which a coronary artery is three-dimensionally modeled by using the information on the voxels corresponding to the coronary region extracted by the coronary-region extraction unit 142. For example, the 3D-coronary-model generation unit 143 generates a 3D coronary model that is a three-dimensional polygon model in which surfaces of the coronary region are represented by a group of polygons. FIG. 3 includes diagrams illustrating one example of generation of the 3D coronary model by the 3D-coronary-model generation unit 143 according to the first embodiment. For example, the 3D-coronary-model generation unit 143 uses the data of the coronary region extracted from the volume data of the CT images to generate a 3D coronary model as depicted in FIG. 3.

The 3D-coronary-model generation unit 143 sends the generated 3D coronary model to a fluid analysis unit 144 described later. The 3D-coronary-model generation unit 143 herein stores positional relation between the generated 3D coronary model and the medical image in a medical-image 3D-coronary-model relative-position storage unit 134. For example, the 3D-coronary-model generation unit 143 stores information on positions (e.g., coordinates) of voxels corresponding to the respective polygons representing the 3D coronary model in the medical-image 3D-coronary-model relative-position storage unit 134. The medical-image 3D-coronary-model relative-position storage unit 134 stores therein positional relation (e.g., coordinate transform matrix) between the 3D coronary model generated by the 3D-coronary-model generation unit 143 and the medical image.

Referring back to FIG. 2, the fluid analysis unit 144 analyzes indices relating to blood flow in blood vessels using the image containing blood vessels collected by the medical-image diagnostic apparatus 200 on the basis of fluid analysis. Specifically, the fluid analysis unit 144 performs fluid analysis on the 3D coronary model generated by the 3D-coronary-model generation unit 143, using various conditions input from a fluid-analysis-initial-condition boundary-condition input unit 111, to analyze pressure distribution, blood velocity distribution, and an FFR value, for example, in a coronary vessel. Herein, the fluid-analysis-initial-condition boundary-condition input unit 111 receives input of conditions (e.g., mass, viscosity, and flow rate of blood, Young's modulus of blood vessel) for simulating an index relating to blood flow in a blood vessel on the basis of fluid analysis. For example, the fluid-analysis-initial-condition boundary-condition input unit 111 receives direct input from an operator. The fluid-analysis-initial-condition boundary-condition input unit 111 herein may acquire the conditions from the database.

Figure 4:
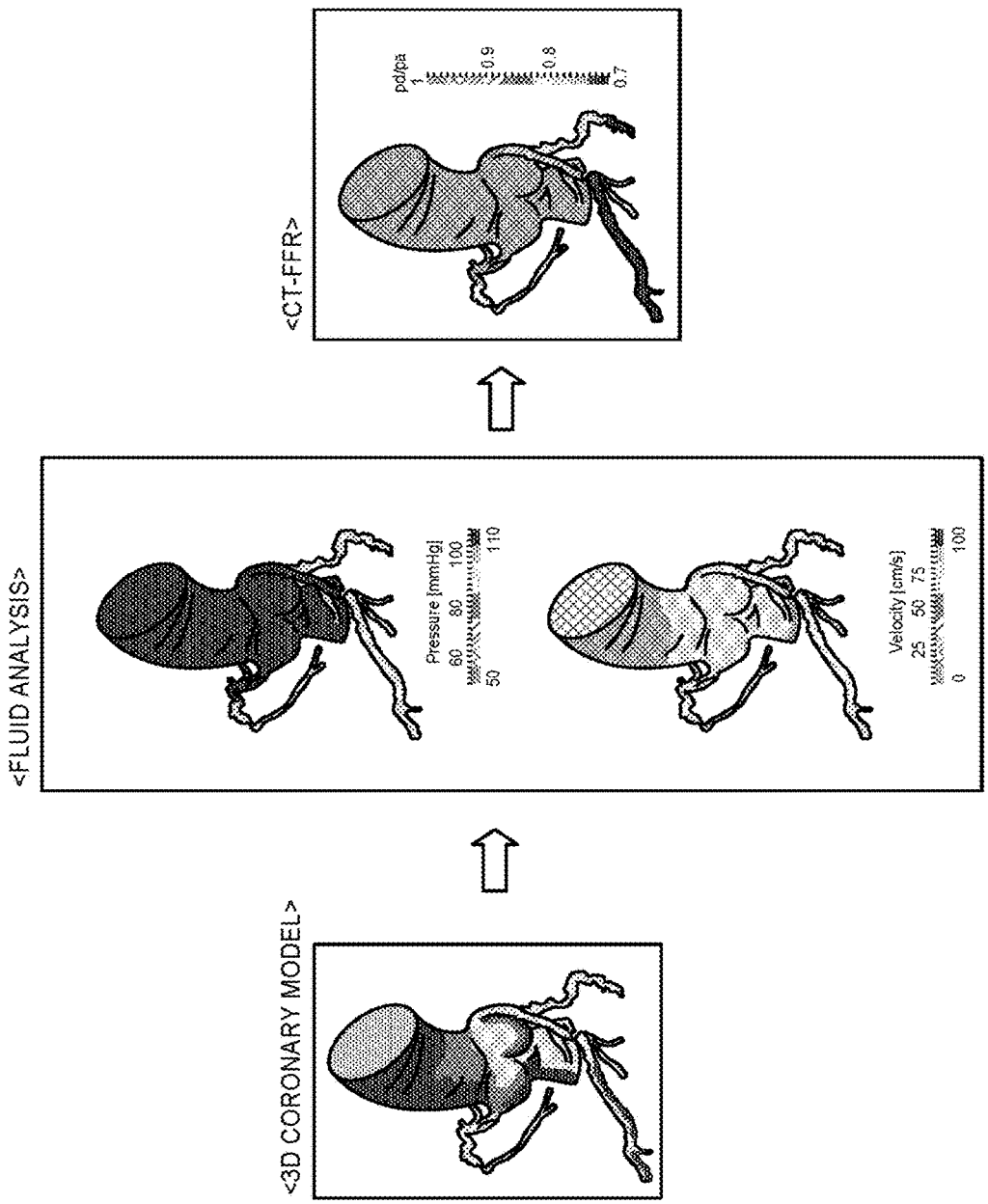
FIG. 4 includes diagrams for explaining one example of analysis performed by a fluid analysis unit according to the first embodiment.

FIG. 4 includes diagrams for explaining one example of analysis performed by the fluid analysis unit 144 according to the first embodiment. For example, as depicted in FIG. 4, the fluid analysis unit 144 performs fluid analysis using the various conditions input by the fluid-analysis-initial-condition boundary-condition input unit 111 on the 3D coronary model generated by the 3D-coronary-model generation unit 143, thereby analyzing the pressure distribution (Pressure (mmHg)) in the 3D coronary model depicted in the central-upper diagram in FIG. 4 and analyzing the blood velocity distribution (Velocity (cm/s)) in the 3D coronary model depicted in the central-lower diagram in FIG. 4.

Furthermore, as depicted in the right diagram in FIG. 4, the fluid analysis unit 144 calculates an FFR value (CT-FFR), for example, in the 3D coronary model from the pressure distribution (Pressure (mmHG)) and the blood velocity distribution (Velocity (cm/s)), for example, in the analyzed 3D coronary model. For example, as depicted in FIG. 4, the fluid analysis unit 144 analyzes an FFR value in each position of the 3D coronary model. The fluid analysis unit 144 then stores a fluid analysis result such as the pressure distribution, the blood velocity distribution, and the FFR value in the 3D coronary model in a fluid-analysis-result storage unit 135. The fluid analysis unit 144 also stores positional relation between the 3D coronary model and the fluid analysis result in a 3D-coronary-model fluid-analysis-result relative-position storage unit 136.

The fluid-analysis-result storage unit 135 stores therein the fluid analysis result obtained by the fluid analysis unit 144. The 3D-coronary-model fluid-analysis-result relative-position storage unit 136 stores therein the positional relation between the fluid analysis result obtained by the fluid analysis unit 144 and the 3D coronary model.

An alignment processing unit 145 identifies the position, on the image, of the index relating to blood flow in a blood vessel analyzed through the fluid analysis using the image containing blood vessels collected by the medical-image diagnostic apparatus 200. Specifically, the alignment processing unit 145 identifies the position, on the image, of the index analyzed through the fluid analysis using the 3D polygon model extracted from the image containing blood vessels. For example, the alignment processing unit 145 identifies the position, on the CT image, of the result of fluid analysis using the 3D coronary model generated by using the coronary arteries extracted from the CT image.

In one example, the alignment processing unit 145 first reads information on positions of voxels corresponding to the coronary region in volume data of a medical image stored by the medical-image coronary-region relative-position storage unit 133 and information on the position of the 3D coronary model in the volume data of the medical image stored by the medical-image 3D-coronary-model relative-position storage unit 134 to identify the position of the 3D coronary model corresponding to the position of the coronary region in the medical image, thereby aligning the coronary region with the 3D coronary model.

The alignment processing unit 145 then reads the position of the fluid analysis result in the 3D coronary model stored by the 3D-coronary-model fluid-analysis-result relative-position storage unit 136, and associates this position with the coronary region with which the fluid analysis result is aligned. In other words, the alignment processing unit 145 identifies the position of the fluid analysis result in the coronary region. The alignment processing unit 145 then sends information on the identified position to a medical-image fluid-analysis-result fusion-image generation unit 146 described later.

As described above, the alignment processing unit 145 aligns a medical image with an anatomical structure model, so that, for example, the medical-image fluid-analysis-result fusion-image generation unit 146 can generate a fusion image in which a simulation result is indicated at an accurate position of a blood vessel contained in the medical image. Herein, a method of alignment is not limited to the above-described method, and any other methods may be used therefor. For example, alignment may be performed with reference to an anatomical landmark of the medical image and the anatomical structure model. In this case, for example, the alignment processing unit 145 aligns a coronary artery contained in volume data of the medical image with the 3D coronary model with reference to the anatomical landmark. The alignment processing unit 145 then associates the position of the fluid analysis result in the 3D coronary model with the coronary artery contained in the volume data to identify the position of the fluid analysis result in the coronary region.

The medical-image fluid-analysis-result fusion-image generation unit 146 displays the position on the image containing blood vessels and also displays the index associated with the position on a display unit 120. Specifically, based on the position of the fluid analysis result in the coronary region aligned by the alignment processing unit 145, the medical-image fluid-analysis-result fusion-image generation unit 146 generates a fusion image in which the fluid analysis result is indicated in the corresponding position of the medical image read from the medical-image storage unit 131, and displays the generated fusion image on the display unit 120.

Figure 5:
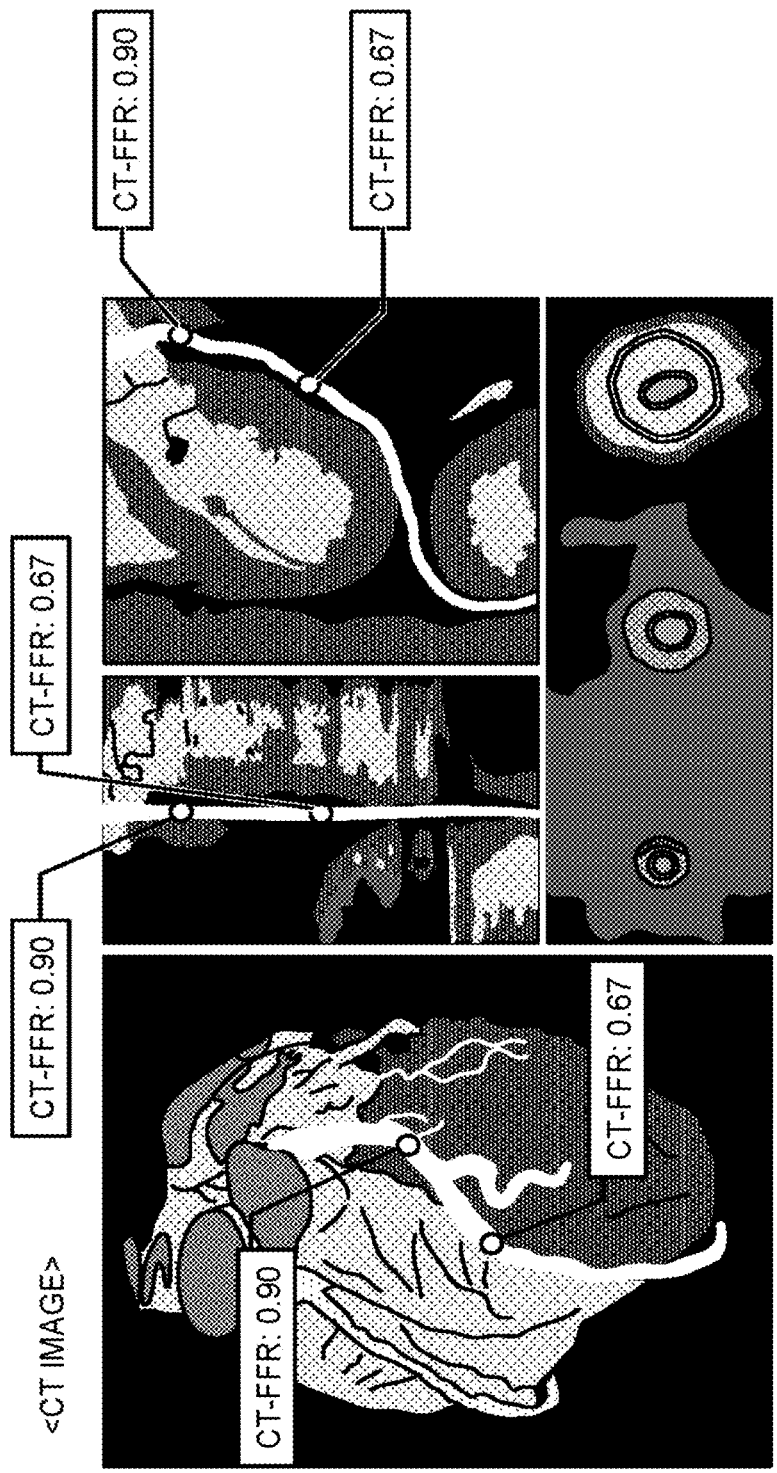
FIG. 5 includes diagrams illustrating one example of fusion images displayed on a display unit according to the first embodiment.

FIG. 5 includes diagrams illustrating one example of fusion images displayed on the display unit 120 according to the first embodiment. For example, the medical-image fluid-analysis-result fusion-image generation unit 146 generates a fusion image in which the fluid analysis results "CT-FFR: 0.90" and "CT-FFR: 0.67" obtained by the fluid analysis unit 144 are associated with positions corresponding to coronary arteries in a CT image of a heart as depicted in the left diagram of FIG. 5, and displays the fusion image on the display unit 120. This operation enables an observer to perform diagnosis while comparing the fluid analysis results with morphological information, so that diagnostic performance can be improved.

Herein, the medical-image fluid-analysis-result fusion-image generation unit 146 can generate not only a volume rendering image but also a fusion image in which the fluid analysis results "CT-FFR: 0.90" and "CT-FFR: 0.67" are associated with positions corresponding to coronary arteries in a curved multi planer reconstruction (CPR) image or an MPR image as depicted in the right-upper row of FIG. 5, for example, and display the fusion images on the display unit 120. The medical-image fluid-analysis-result fusion-image generation unit 146 can also generate a fusion image in which a fluid analysis result such as pressure distribution is indicated in a cross section (CS) image of coronary arteries as depicted in the right-lower row of FIG. 5, for example, and display the fusion image on the display unit 120. In this manner, the medical-image fluid-analysis-result fusion-image generation unit 146 can generate various images from the original volume data, and can generate and display fusion images in which the fluid analysis results are displayed on the generated images. Herein, the fluid analysis results to be indicated on a medical image can be optionally selected and, for example, it is possible to indicate difference of pressure distribution in coronary arteries in different colors, and generate and display a fusion image in which FFR values are indicated in the respective positions of the coronary arteries.

Figure 6:
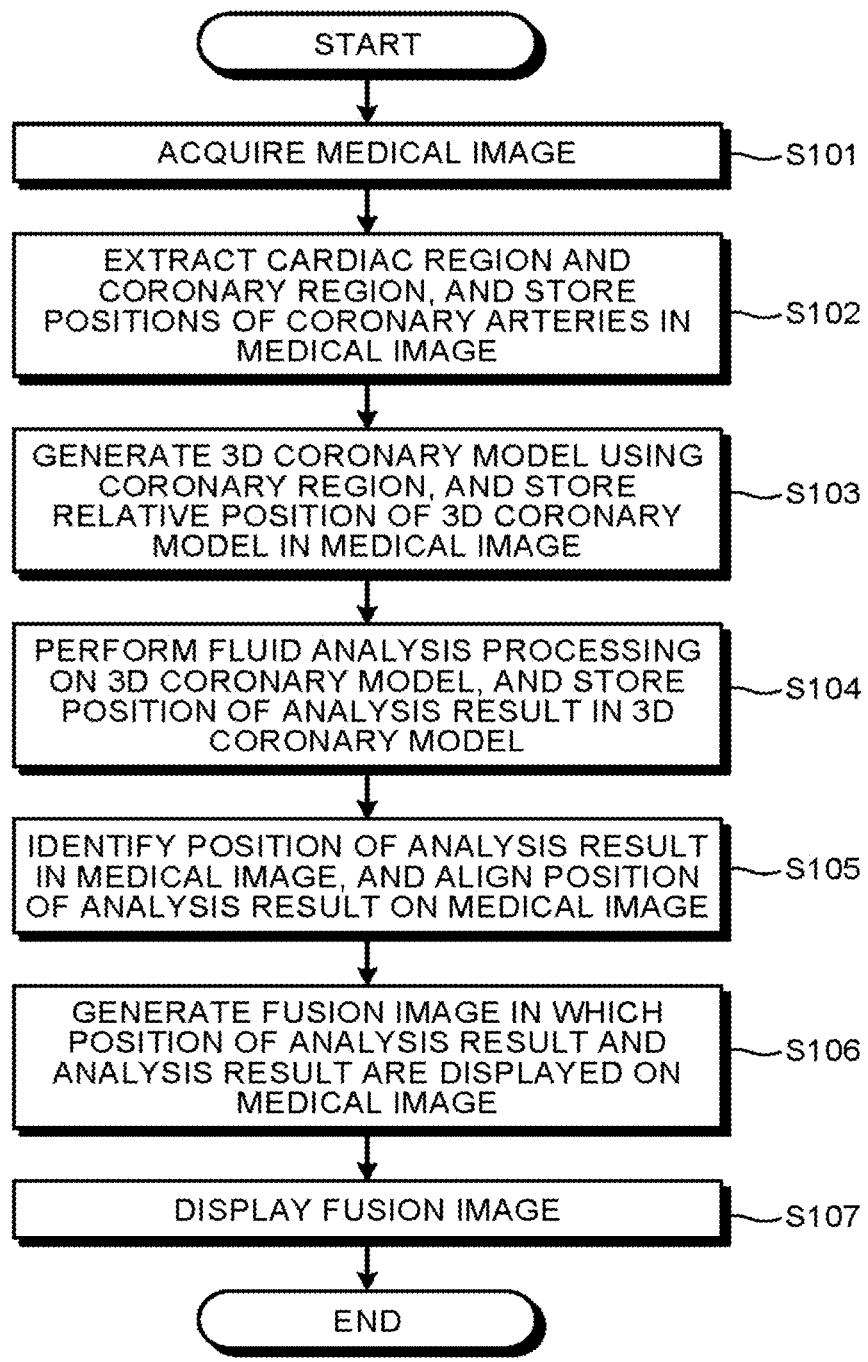
FIG. 6 is a flowchart illustrating the procedure of processing performed by the medical-image processing apparatus according to the first embodiment.

FIG. 6 is a flowchart illustrating the procedure of processing performed by the medical-image processing apparatus 100 according to the first embodiment. In FIG. 6, a case is illustrated in which a fluid analysis result based on a 3D coronary model generated from a medical image is indicated on a CT image. As depicted in FIG. 6, in the medical-image processing apparatus 100 according to the first embodiment, the medical-image input unit 110 acquires a medical image (step S101), and the cardiac-region extraction unit 141 and the coronary-region extraction unit 142 extract a cardiac region in the medical image and a coronary region in the cardiac region, respectively. The coronary-region extraction unit 142 then causes the medical-image coronary-region relative-position storage unit 133 to store therein positions of coronary arteries in the medical image (step S102).

Subsequently, the 3D-coronary-model generation unit 143 generates a 3D coronary model using the extracted coronary region, and causes the medical-image 3D-coronary-model relative-position storage unit 134 to store therein the relative position of the 3D coronary model in the medical image (step S103). Furthermore, the fluid analysis unit 144 performs fluid analysis processing on the generated 3D coronary model, and causes the 3D-coronary-model fluidanalysis-result relative-position storage unit 136 to store therein the position of the analysis result in the 3D coronary model (step S104).

The alignment processing unit 145 then identifies the position of the analysis result in the medical image on the basis of the positions of the coronary arteries in the medical image stored in the medical-image coronary-region relative-position storage unit 133, the relative position of the 3D coronary model in the medical image stored in the medical-image 3D-coronary-model relative-position storage unit 134, and the position of the analysis result in the 3D coronary model stored in the 3D-coronary-model fluid-analysis-result relative-position storage unit 136 to align the position of the analysis result on the medical image (step S105).

Subsequently, the medical-image fluid-analysis-result fusion-image generation unit 146 generates a fusion image in which the position of the analysis result and the analysis result are displayed on the medical image (step S106), and displays the generated fusion image on the display unit 120 (step S107).

As described above, according to the first embodiment, the alignment processing unit 145 identifies the position, on the image, of the index relating to blood flow in a blood vessel analyzed through fluid analysis using the image containing the blood vessels collected by the medical-image diagnostic apparatus 200. The medical-image fluid-analysis-result fusion-image generation unit 146 displays the position on the image containing the blood vessels and also displays the index associated with the position on the display unit 120. Thus, the medical-image processing apparatus 100 according to the first embodiment can display the analysis result based on the fluid analysis at an accurate position in the medical image, and makes it possible to easily compare the result based on the fluid analysis with the medical image.

Consequently, a morphological state of blood vessels can be easily checked, whereby diagnostic performance can be improved. For example, if an FFR value is small in the analysis result based on the fluid analysis, the degree of stenosis on this stenosis can be easily checked visually.

Furthermore, according to the first embodiment, the alignment processing unit 145 identifies the position, on the image, of the index analyzed through fluid analysis using a three-dimensional polygon model extracted from the image containing blood vessels. Thus, the medical-image processing apparatus 100 according to the first embodiment makes it possible to easily identify the position by using existing techniques.

Figure 7:
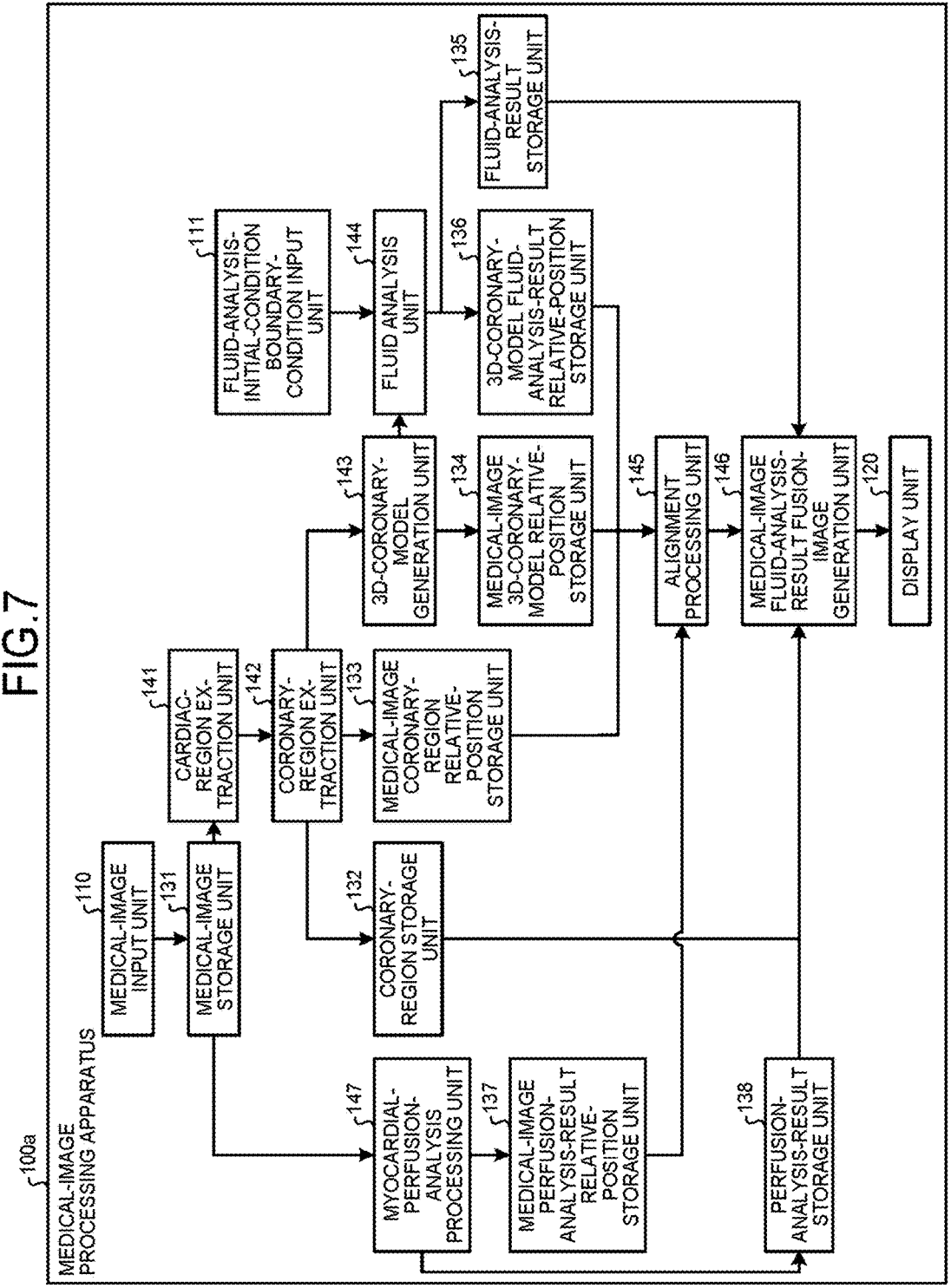
FIG. 7 is a diagram illustrating one example of configuration of a medical-image processing apparatus according to a second embodiment.

In a second embodiment, a case will be described in which a fusion image in which a fluid analysis result is indicated on an analysis image obtained by analyzing a medical image is generated and displayed. FIG. 7 is a diagram illustrating one example of configuration of a medical-image processing apparatus 100a according to the second embodiment. In the second embodiment, a case of using a perfusion image as the analysis image will be described. As depicted in FIG. 7, the medical-image processing apparatus 100a according to the second embodiment is different from the medical-image processing apparatus 100 according to the first embodiment depicted in FIG. 2 in additionally having a myocardial-perfusion-analysis processing unit 147, a medical-image perfusion-analysis-result relative-position storage unit 137, and a perfusion-analysis-result storage unit 138 and also in processing performed by the alignment processing unit 145 and the medical-image fluid-analysis-result fusion-image generation unit 146. The following describes these differences focusing thereon.

The myocardial-perfusion-analysis processing unit 147 performs myocardial perfusion analysis using a medical image stored by the medical-image storage unit 131. Specifically, the myocardial-perfusion-analysis processing unit 147 calculates temporal concentration changes of a CT value based on CT images obtained by imaging on a time-series basis a cardiac region of a subject to whom a contrast agent is administered. The myocardial-perfusion-analysis processing unit 147 then generates a perfusion image in which an index representing a dynamic behavior of blood flow passing through a capillary in a tissue is mapped on the tissue from the calculated temporal concentration changes of the CT value.

The myocardial-perfusion-analysis processing unit 147 then stores information on each position of the perfusion analysis result (index representing dynamic behavior of blood flow passing through the capillary) in the medical image in the medical-image perfusion-analysis-result relative-position storage unit 137. The myocardial-perfusion-analysis processing unit 147 also stores the generated perfusion image in the perfusion-analysis-result storage unit 138.

The medical-image perfusion-analysis-result relative-position storage unit 137 stores therein the information on each position of the perfusion analysis result in volume data of the medical image. The perfusion-analysis-result storage unit 138 stores therein the perfusion image.

The alignment processing unit 145 according to the second embodiment identifies the position of the index on an analysis image generated based on the medical image. Specifically, the alignment processing unit 145 identifies the position, on the analysis image, of the index analyzed through fluid analysis using a 3D polygon model. For example, the alignment processing unit 145 identifies the position, on the perfusion image, of the result of fluid analysis using a 3D coronary model generated by using coronary arteries extracted from a CT image.

In one example, the alignment processing unit 145 first reads information on each position of the perfusion analysis result in volume data of a medical image stored by the medical-image perfusion-analysis-result relative-position storage unit 137, information on the positions of voxels corresponding to the coronary region in the volume data of the medical image, and information on the position of the 3D coronary model in the volume data of the medical image to identify relative positions between the respective pieces of information, thereby aligning the perfusion analysis result with the coronary region and with the 3D coronary model in the medical image.

The alignment processing unit 145 then identifies the position of the fluid analysis result in the coronary region for which the perfusion analysis result is aligned with the coronary region and with the 3D coronary model in the medical image. The alignment processing unit 145 then sends information on the identified position to the medical-image fluid-analysis-result fusion-image generation unit 146.

The medical-image fluid-analysis-result fusion-image generation unit 146 according to the second embodiment displays the position on the analysis image and also displays the index associated with the position on the display unit 120. Specifically, based on the perfusion analysis result, the coronary region, and the 3D coronary model that are aligned in the medical image by the alignment processing unit 145, and based on the position of the fluid analysis result in the coronary region, the medical-image fluid-analysis-result fusion-image generation unit 146 generates a fusion image in which the fluid analysis result is indicated in the corresponding position of the perfusion image read from the perfusion-analysis-result storage unit 138, and displays the generated fusion image on the display unit 120.

Figure 8:
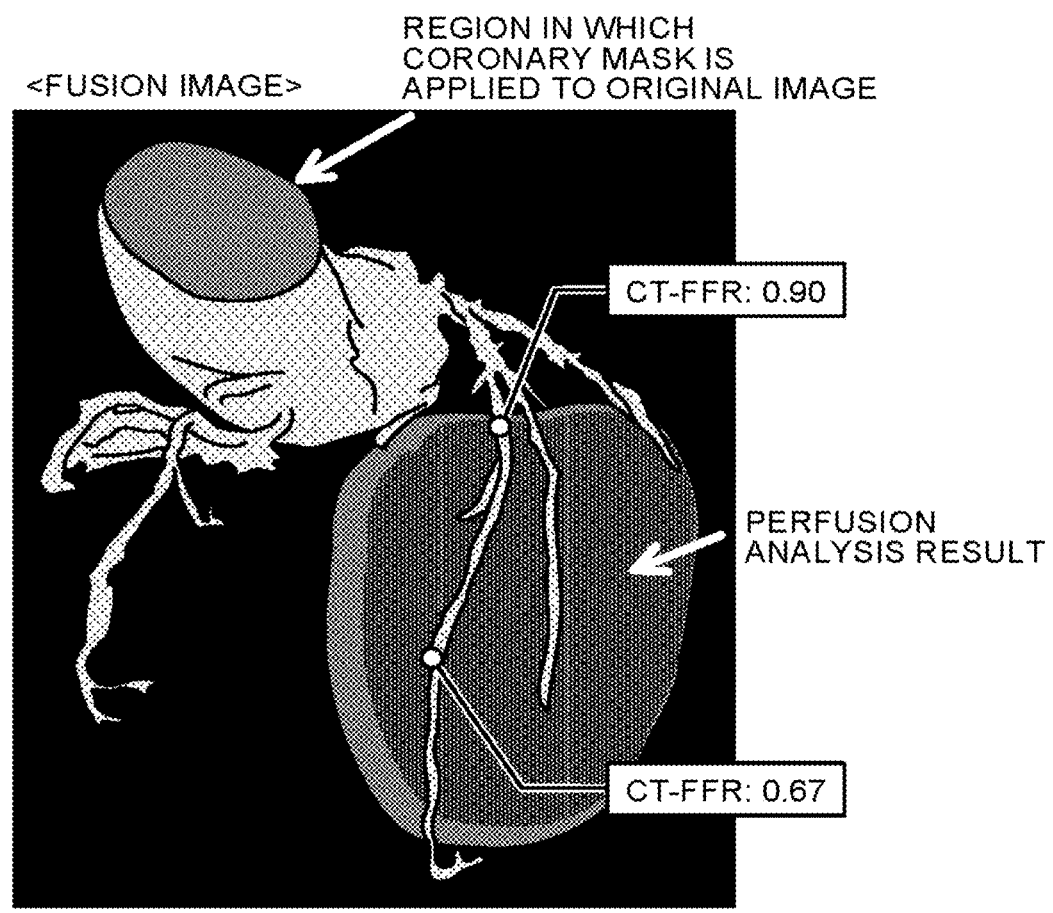
FIG. 8 is a diagram illustrating one example of a fusion image displayed on a display unit according to the second embodiment.

FIG. 8 is a diagram illustrating one example of the fusion image displayed on the display unit 120 according to the second embodiment. For example, the medical-image fluid-analysis-result fusion-image generation unit 146 generates a fusion image in which the fluid analysis results "CT-FFR: 0.90" and "CT-FFR: 0.67" obtained by the fluid analysis unit 144 are associated with positions corresponding to coronary arteries in a perfusion image of a cardiac region as depicted in FIG. 8, and displays the fusion image on the display unit 120.

Figure 9:
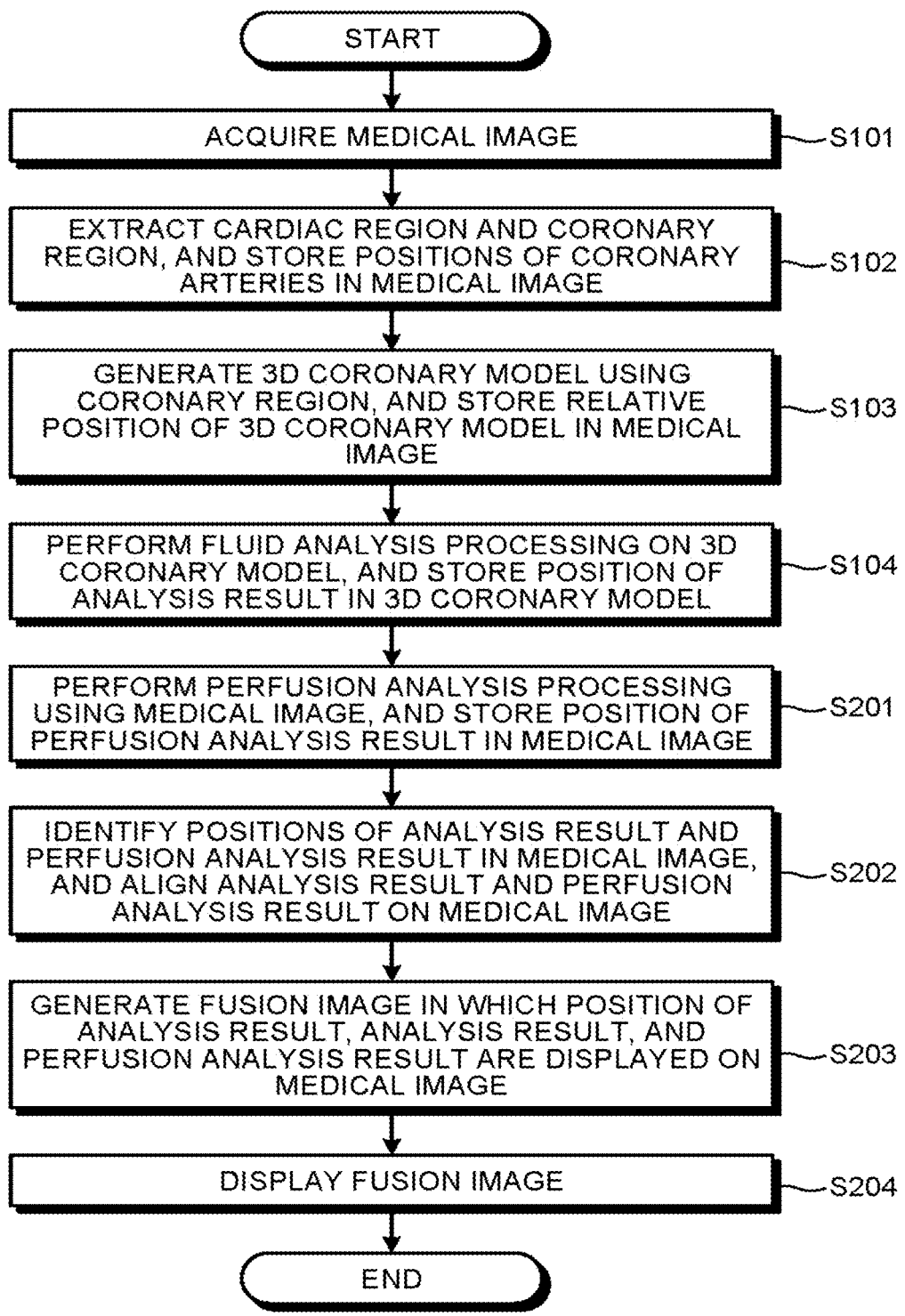
FIG. 9 is a flowchart illustrating the procedure of processing performed by the medical-image processing apparatus according to the second embodiment.

FIG. 9 is a flowchart illustrating the procedure of processing performed by the medical-image processing apparatus 100a according to the second embodiment. In FIG. 9 the same step numbers are given to the same processes as those of the flowchart depicted in FIG. 6, and thus a detail description thereof is omitted. As depicted in FIG. 9, in the medical-image processing apparatus 100a according to the second embodiment, a medical image is acquired (step S101), positions of coronary arteries in the medical image are stored (step S102), the relative position of a 3D coronary model in the medical image is stored (step S103), and the position of the analysis result in the 3D coronary model is stored (step S104).

Subsequently, the myocardial-perfusion-analysis-processing unit 147 performs perfusion analysis processing using the medical image, and causes the medical-image perfusion-analysis-result relative-position storage unit 137 to store therein the position of the perfusion analysis result in the medical image (step S201). The alignment processing unit 145 then identifies the positions of the analysis result and the perfusion analysis result in the medical image on the basis of the perfusion analysis results stored in the medical-image perfusion-analysis-result relative-position storage unit 137, the positions of the coronary arteries in the medical image stored in the medical-image coronary-region relative-position storage unit 133, the relative position of the 3D coronary model in the medical image stored in the medical-image 3D-coronary-model relative-position storage unit 134, and the position of the analysis result in the 3D coronary model stored in the 3D-coronary-model fluid-analysis-result relative-position storage unit 136 to align the positions of the analysis result and the perfusion analysis result on the medical image (step S202).

Subsequently, the medical-image fluid-analysis-result fusion-image generation unit 146 generates a fusion image in which the position of the analysis result, the analysis result, and the perfusion analysis result are displayed on the medical image (step S203), and displays the generated fusion image on the display unit 120 (step S204).

As described above, according to the second embodiment, the alignment processing unit 145 identifies the position of the index on the perfusion image generated based on the medical image. The medical-image fluid-analysis-result fusion-image generation unit 146 displays the position on the perfusion image, and also displays the index associated with the position on the display unit 120. Thus, the medical-image processing apparatus 100a according to the second embodiment makes it possible to easily compare the result based on the fluid analysis with the analysis image based on the medical image. Consequently, diagnostic performance can be further improved. For example, if ischemia is observed in a perfusion image, the FFR value of the blood vessel responsible therefor can be easily checked.

Figure 10:
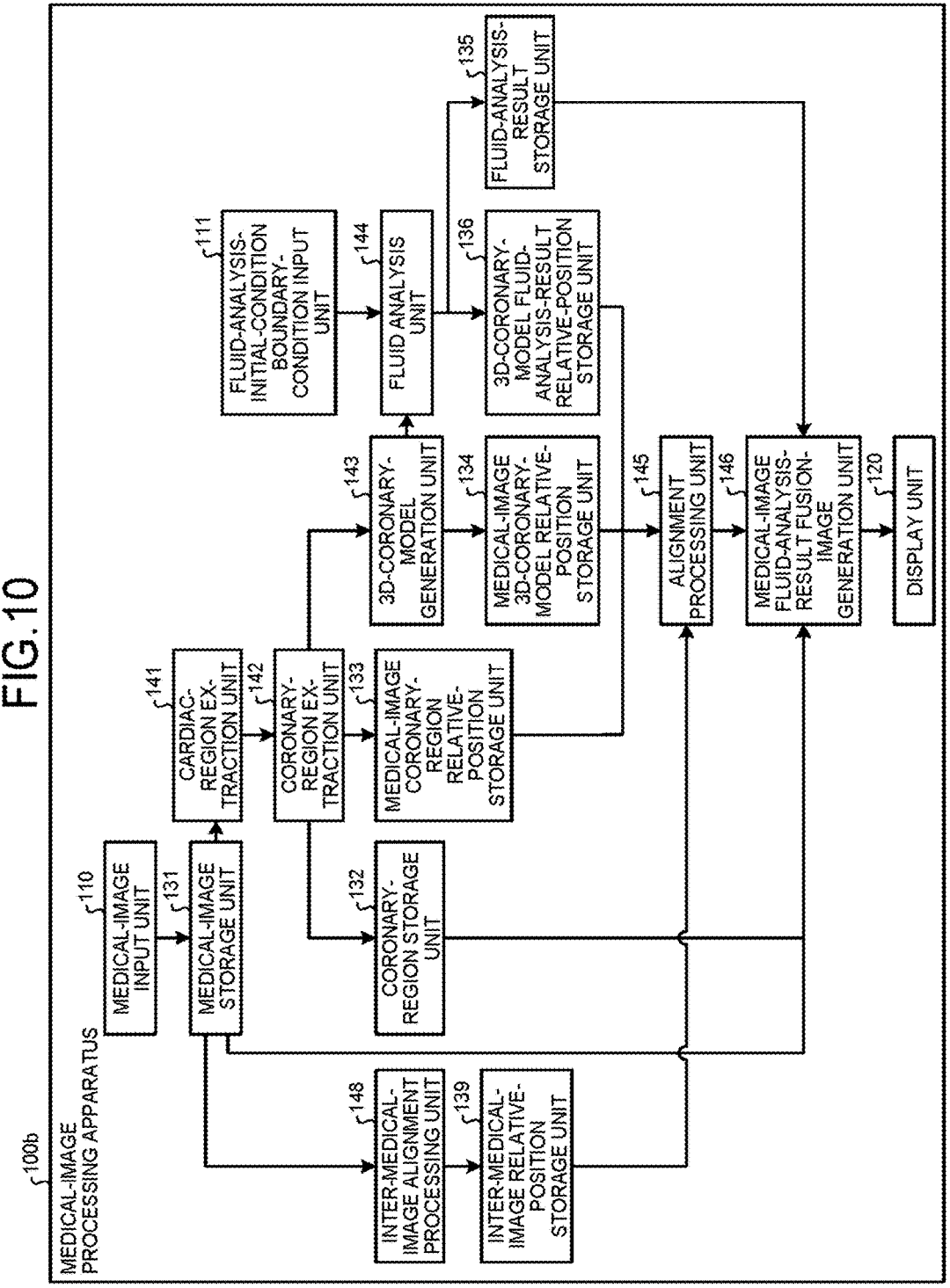
FIG. 10 is a diagram illustrating one example of configuration of a medical-image processing apparatus according to a third embodiment.

In a third embodiment, a case will be described in which analysis results based on fluid analysis are indicated on different medical images. FIG. 10 is a diagram illustrating one example of configuration of a medical-image processing apparatus 100b according to the third embodiment. In the third embodiment, a case of indicating an analysis result obtained by fluid analysis using a 3D coronary model generated from a CT image on an MR image will be described as an example. As depicted in FIG. 10, the medical-image processing apparatus 100b according to the third embodiment is different from the medical-image processing apparatus 100 according to the first embodiment depicted in FIG. 2 in additionally having an inter-medical-image alignment processing unit 148 and an inter-medical-image relative-position storage unit 139 and also in processing performed by the alignment processing unit 145 and the medical-image fluid-analysis-result fusion-image generation unit 146. The following describes these differences focusing thereon.

The inter-medical-image alignment processing unit 148 performs alignment between different medical images stored by the medical-image storage unit 131. For example, the inter-medical-image alignment processing unit 148 performs alignment between a CT image and an MR image in both of which a cardiac region of the same subject is imaged. Herein, the processing of the alignment between the medical images by the inter-medical-image alignment processing unit 148 can be performed by existing known techniques and, for example, by examining similarity of voxels between two medical images, alignment of the image is performed. The inter-medical-image relative-position storage unit 139 stores therein information on alignment between different medical images performed by the inter-medical-image alignment processing unit 148.

The alignment processing unit 145 according to the third embodiment performs alignment between medical images containing blood vessels collected by different types of medical-image diagnostic apparatus to identify positions of indices on the different types of images. Specifically, the alignment processing unit 145 identifies positions, on different medical images, of indices analyzed through fluid analysis using a 3D polygon model. For example, the alignment processing unit 145 identifies the position, on an MR image, of the fluid analysis result obtained by using a 3D coronary model generated by using coronary arteries extracted from a CT image.

In one example, the alignment processing unit 145 first reads information on alignment between a CT image and an MR image stored by the inter-medical-image relative-position storage unit 139, information on positions of voxels corresponding to a coronary region in volume data of the CT image, and information on the position of a 3D coronary model in the volume data of the CT image to identify relative positions of the respective pieces of information, thereby performing alignment between the coronary region in the MR image and the 3D coronary model.

The alignment processing unit 145 then identifies the position of the fluid analysis result in the coronary region for which alignment between the coronary region in the MR image and the 3D coronary model is performed. The alignment processing unit 145 then sends information on the identified position to the medical-image fluid-analysis-result fusion-image generation unit 146.

The medical-image fluid-analysis-result fusion-image generation unit 146 according to the third embodiment displays the position on different types of images and also displays the index associated with the position on the display unit 120. Specifically, based on the coronary region in the MR image and the 3D coronary model that are aligned by the alignment processing unit 145, and also based on the position of the fluid analysis result in the coronary region, the medical-image fluid-analysis-result fusion-image generation unit 146 generates a fusion image in which the fluid analysis result is indicated at the corresponding position on the MR image read from the medical-image storage unit 131, and displays the generated fusion image on the display unit 120.

Figure 11:
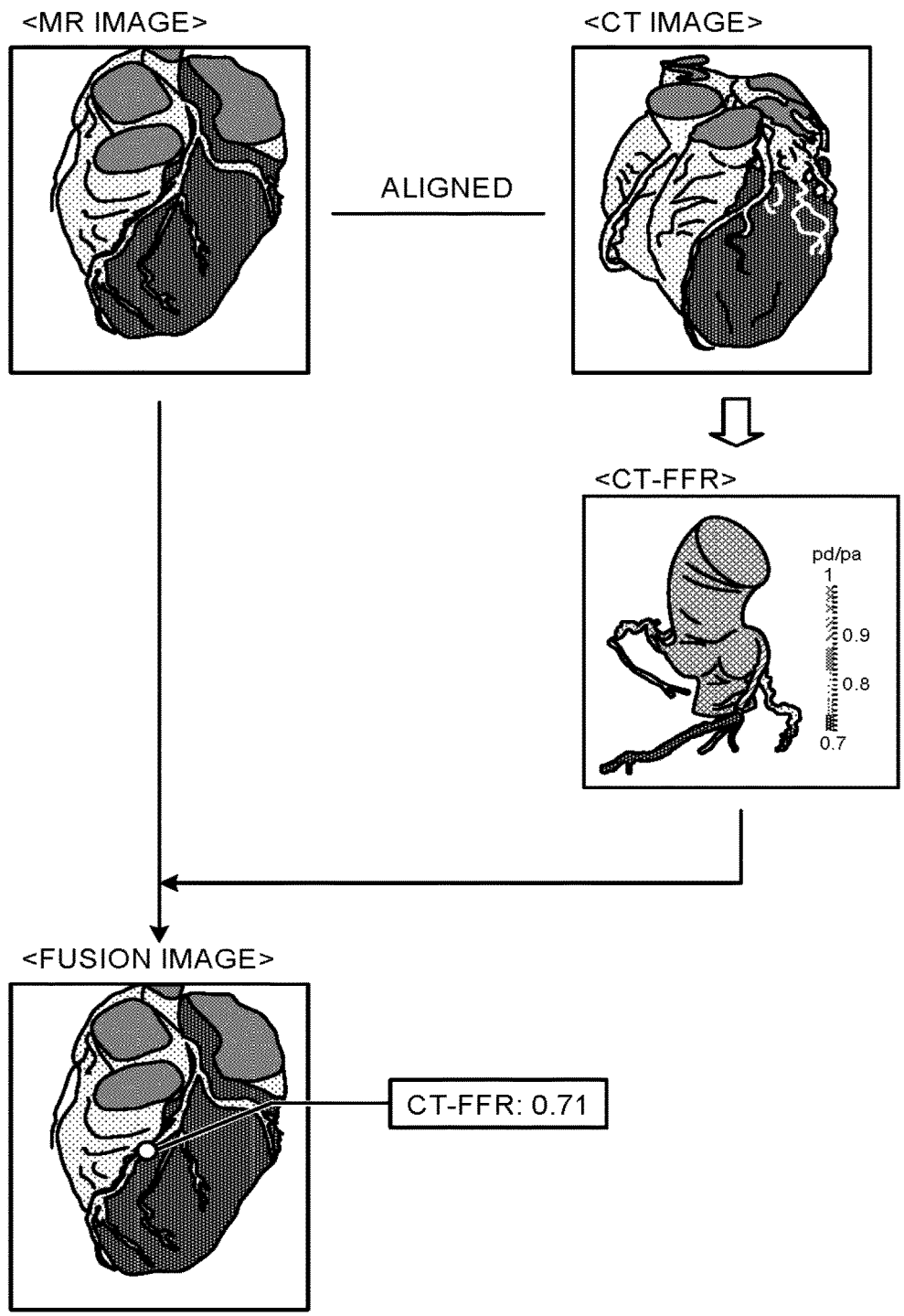
FIG. 11 includes diagrams illustrating one example of a fusion image displayed on a display unit according to the third embodiment.

FIG. 11 includes diagrams illustrating one example of the fusion image displayed on the display unit 120 according to the third embodiment. For example, as depicted in FIG. 11, the medical-image fluid-analysis-result fusion-image generation unit 146 generates a fusion image in which the fluid analysis result "CT-FFR: 0.71" of a 3D coronary model generated from a CT image at a corresponding position on the MR image aligned with the CT image, and displays the fusion image on the display unit 120. This operation makes it possible to compare medical images that are collected by different modalities with the fluid analysis result, and thus diagnostic performance can be improved. The above-described example is merely an example and the medical images to be used are not limited to the above-described ones, and any types of medical images can be used.

In the above-described examples, a case of displaying a fusion image has been described in which a fluid analysis result is indicated on an original image of an MR image, but the medical-image processing apparatus 100*b* according to the present embodiment can generate and display a fusion image in which the fluid analysis result is indicated on an analysis image of the MR image. For example, the medical-image processing apparatus 100*b* depicted in FIG. 10 further includes the myocardial-perfusion-analysis processing unit 147, the medical-image perfusion-analysis-result relative-position storage unit 137, and the perfusion-analysis-result storage unit 138 depicted in FIG. 7. The alignment processing unit 145 performs alignment with the analysis image, and the medical-image fluid-analysis-result fusion-image generation unit 146 generates a fusion image in which the fluid analysis result is indicated on the analysis image to display the fusion image on the display unit 120.

Figure 12:
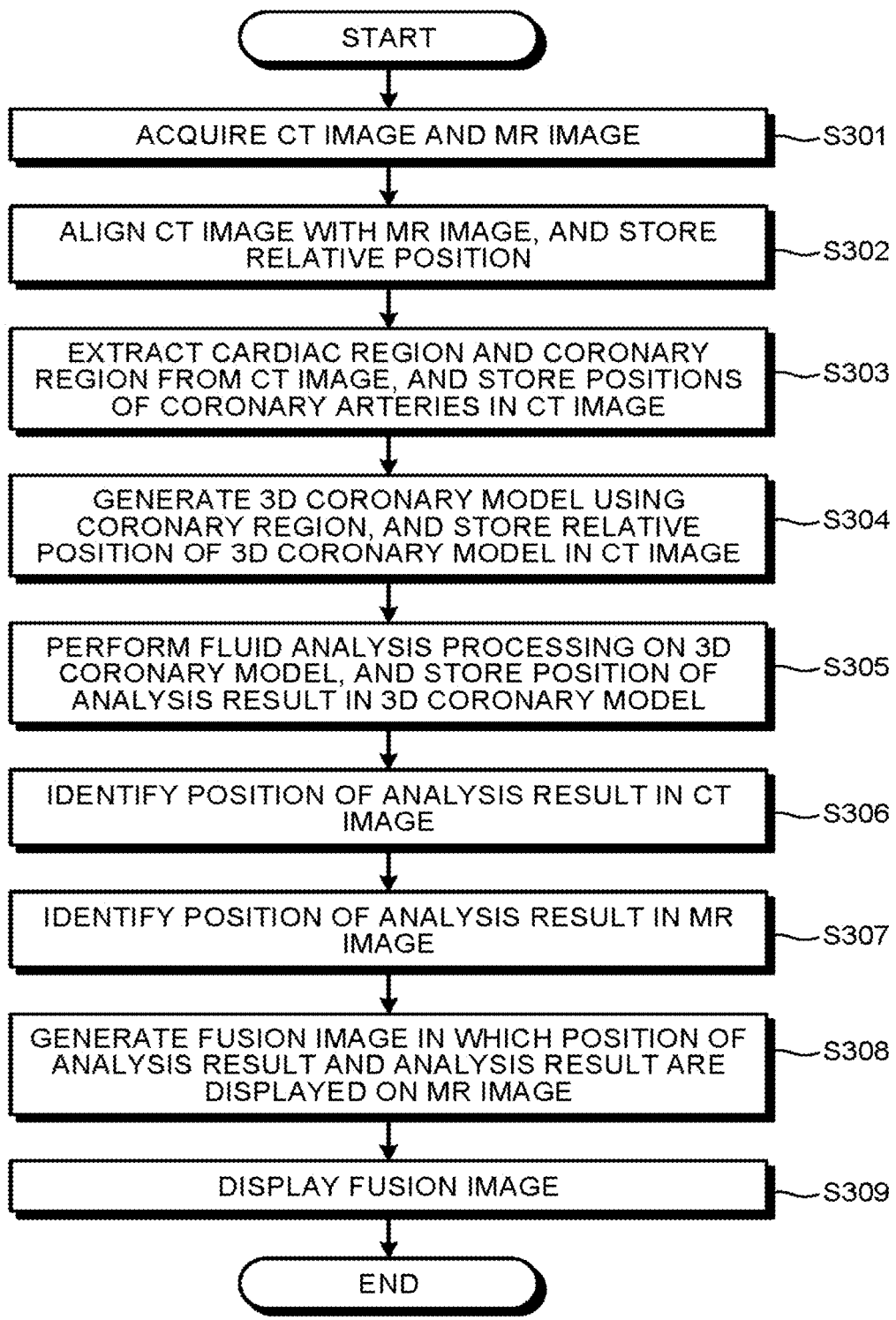
FIG. 12 is a flowchart illustrating the procedure of processing performed by the medical-image processing apparatus according to the third embodiment.

FIG. 12 is a flowchart illustrating the procedure of processing performed by the medical-image processing apparatus 100*b* according to the third embodiment. In FIG. 12, a case is illustrated in which fluid analysis results based on a 3D coronary model generated from a CT image is indicated on an MR image. As depicted in FIG. 12, in the medical-image processing apparatus 100*b* according to the third embodiment, the medical-image input unit 110 acquires a CT image and an MR image (step S301), the inter-medical-image alignment processing unit 148 aligns the CT image with the MR image and stores the relative position in the inter-medical-image relative-position storage unit 139 (step S302).

The cardiac-region extraction unit 141 and the coronary-region extraction unit 142 then extract a cardiac region in the CT image and a coronary region in the cardiac region, respectively. The coronary-region extraction unit 142 then stores positions of coronary arteries in the CT image in the medical-image coronary-region relative-position storage unit 133 (step S303).

Subsequently, the 3D-coronary-model generation unit 143 generates a 3D coronary model using the extracted coronary region, and stores the relative position of the 3D coronary region in the CT image in the medical-image 3D-coronary-model relative-position storage unit 134 (step S304). Furthermore, the fluid analysis unit 144 performs fluid analysis processing on the generated 3D coronary model, and stores the position of the analysis result in the 3D coronary model in the 3D-coronary-model fluid-analysis-result relative-position storage unit 136 (step S305).

The alignment processing unit 145 then identifies the position of the analysis result in the CT image on the basis of the positions of coronary arteries in the CT image, the relative position of the 3D coronary model in the CT image, and the position of the analysis result in the 3D coronary model (step S306). Furthermore, the alignment processing unit 145 identifies the position of the analysis result in the MR image on the basis of information on the alignment between the CT image and the MR image and the position of the analysis result in the MR image (step S307).

Subsequently, the medical-image fluid-analysis-result fusion-image generation unit 146 generates a fusion image in which the position of the analysis result and the analysis result are displayed on the MR image (step S308), and displays the generated fusion image on the display unit 120 (step S309).

As described above, according to the third embodiment, the alignment processing unit 145 performs alignment between different types of medical images collected by different types of medical-image diagnostic apparatus, thereby identifying the position of an index on the different medical images. The medical-image fluid-analysis-result fusion-image generation unit 146 displays the position on the different medical images and also displays the index associated with the position on the display unit 120. Thus, the medical-image processing apparatus 100*b* according to the third embodiment can display the fluid analysis result on various medical images, and enables diagnostic performance to be further improved.

Embodiments are not limited to the above-described embodiments, and can be implemented in other various forms.

In the above-described embodiments, cases have been described in which a fluid analysis result is displayed on a medical image or an analysis image. However, the embodiments are not limited to these cases, and may be cases of displaying information that is indicated in combination with an analysis result obtained by analyzing a medical image and a fluid analysis result. Specifically, the medical-image fluid-analysis-result fusion-image generation unit 146 according to the fourth embodiment displays evaluation information that is derived from an analysis result obtained by analyzing an index relating to blood flow and an analysis image, in association with the position of the index on the analysis image. For example, it is possible to combine myocardial abnormality evaluated by myocardial perfusion with a CT-FFR value, define the stenosis treatment level according to these states, and display the level on the analysis image.

In one example, the stenosis treatment level is defined based on the myocardial abnormality in a blood-vessel dominant region and the CT-FFR value. The stenosis treatment level herein can be optionally set, and can be set as, for example, "Level 1: myocardial abnormality & FFR<0.75", "Level 2: myocardial abnormality & FFR≥0.75", "Level 3: myocardial normality & FFR<0.75", and "Level 4: myocardial normality & FFR≥0.75". The medical-image fluid-analysis-result fusion-image generation unit 146 reads a perfusion analysis result from the medical-image perfusion-analysis-result relative-position storage unit 137, extracts an index representing hemodynamics in the dominant region for each position of blood vessels, and associates the index with the CT-FFR value.

Figure 13:
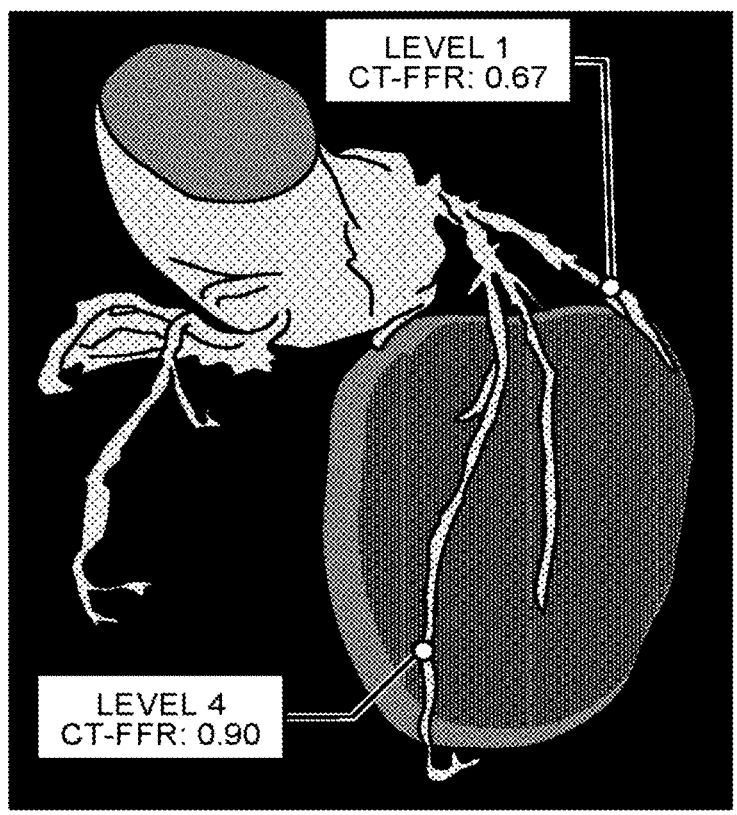
FIG. 13 is a diagram illustrating one example of a fusion image displayed on a display unit according to a fourth embodiment.

The medical-image fluid-analysis-result fusion-image generation unit 146 then refers to the above-described stenosis treatment level, generates a fusion image in which corresponding levels are indicated for the respective positions of the blood vessels, and displays the generated fusion image on the display unit 120. FIG. 13 is a diagram illustrating one example of the fusion image displayed on the display unit 120 according to the fourth embodiment. For example, as depicted in FIG. 13, the medical-image fluid-analysis-result fusion-image generation unit 146 generates a fusion image in which the stenosis treatment levels "Level 1 CT-FFR: 0.67" and "Level 4 CT-FFR: 0.90" are associated with the corresponding positions of the coronary arteries in the perfusion image of the cardiac region, and displays the fusion image on the display unit 120.

Herein, the medical-image fluid-analysis-result fusion-image generation unit 146 may indicate the stenosis treatment levels by indicating numbers for the levels in the image as depicted in FIG. 13 or, alternatively, may display the levels in different colors. For example, the medical-image fluid-analysis-result fusion-image generation unit 146 displays Level 1 emphatically in red, and displays Level 4 in blue. This operation enables an operator to observe a plurality of analysis results using medical images as an integrated evaluation result.

Figure 14A:
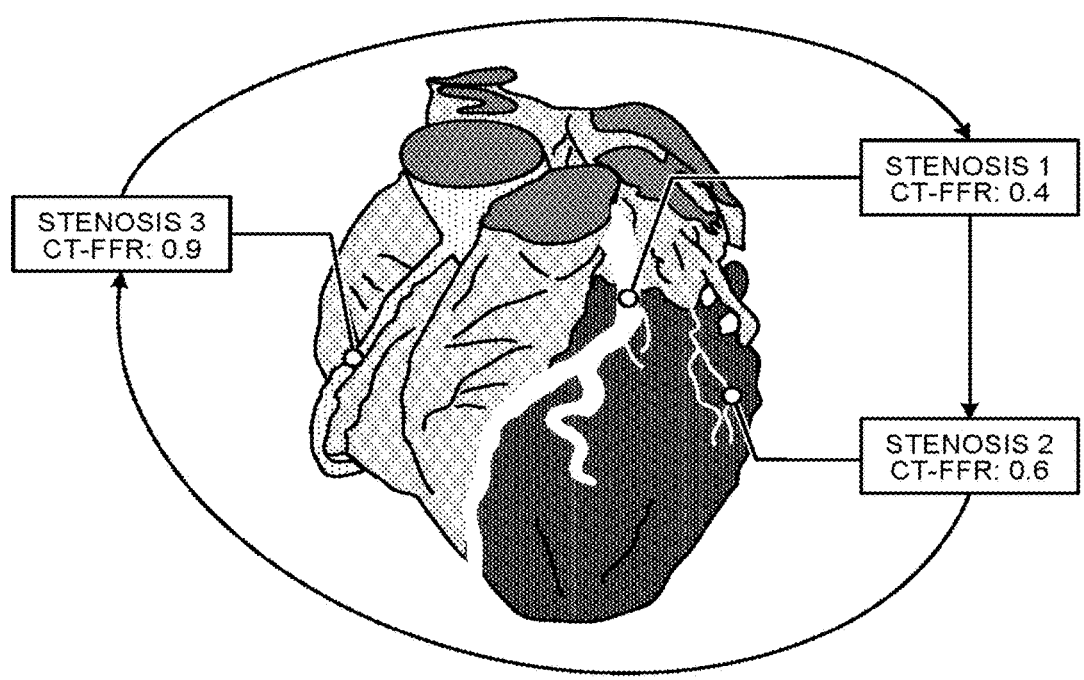
FIG. 14A is a diagram illustrating one example of a fusion image displayed on the display unit according to the fourth embodiment.
Figure 14B:
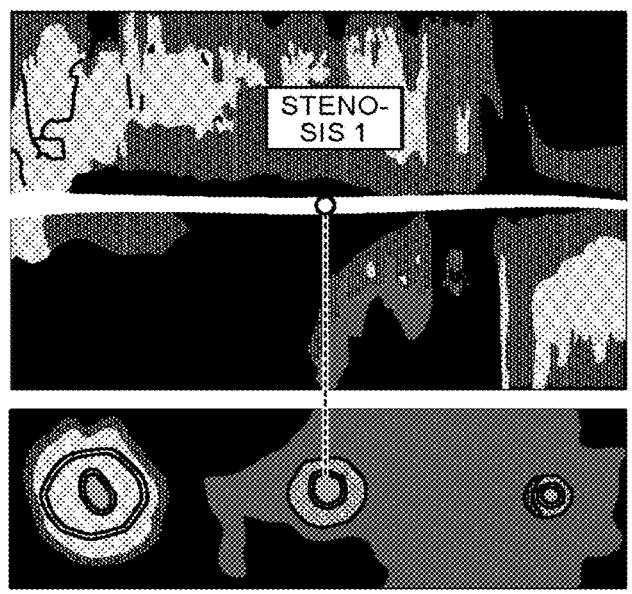
FIG. 14B is a diagram illustrating one example of a fusion image displayed on the display unit according to the fourth embodiment.

Display by the medical-image processing apparatus 100 is not limited to the above-described examples, and display can be performed in various other manners. For example, the medical-image fluid-analysis-result fusion-image generation unit 146 can perform display in various manners for each stenosis. FIGS. 14A and 14B are diagrams each illustrating one example of a fusion image displayed on a display unit according to the fourth embodiment. For example, as depicted in FIG. 14A, the medical-image fluid-analysis-result fusion-image generation unit 146 can display each of "Stenosis 1: CT-FFR: 0.4", "Stenosis 2: CT-FFR: 0.6", and "Stenosis 3: CT-FFR: 0.9" for each stenosis in a switched manner. In FIG. 14A, all stenoses are illustrated but, actually, each stenosis is displayed one by one.

In this case, for example, the medical-image fluid-analysis-result fusion-image generation unit 146 makes a list of stenotic portions in the ascending order of CT-FFR values, and displays them one by one in the order of the list in response to operation of an operator. This operation allows the operator to observe the peripheries of the stenoses in the ascending order of CT-FFR values and check the status. The list of stenotic portions can be made in any order, and may be made in the descending order. Making of the list of stenotic portions may be performed for all stenoses, but the making may be performed only for stenoses the CT-FFR values of which are smaller than or equal to a cutoff value for CT-FFR values after setting the cutoff value in advance.

Furthermore, for example, the medical-image fluid-analysis-result fusion-image generation unit 146 can generate a CPR image and a CS image from volume data for the stenosis 1 to display the generated images associated with each other as depicted in FIG. 14B, thereby performing a more detailed check, which can be used also for a prior check when a stent is placed.

Furthermore, in the above-described third embodiment, a case has been described in which a CT image and an MR image that are obtained by imaging a cardiac region of the same subject are used and a fluid analysis result based on a three-dimensional polygon model generated from the CT image is combined with the MR image, but the embodiments are not limited to this case, and various other medical images can be used therefor.

Figure 15:
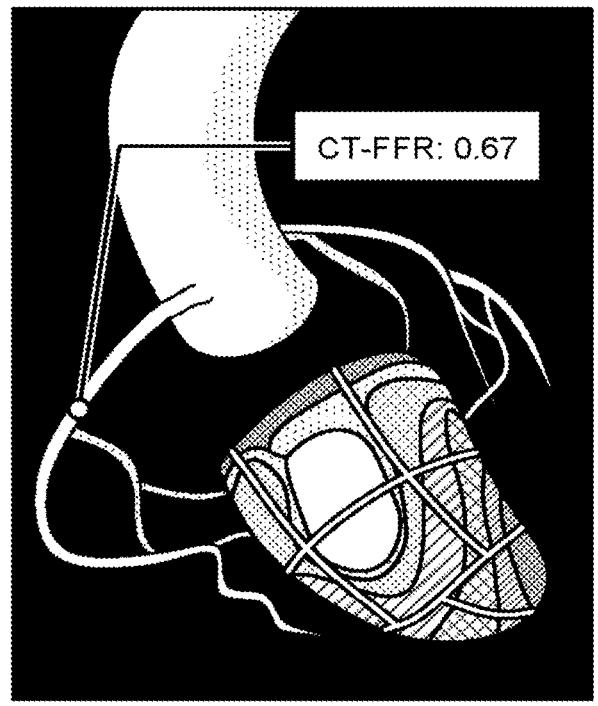
FIG. 15 is a diagram illustrating one example of a fusion image displayed on the display unit according to the fourth embodiment.

FIG. 15 is a diagram illustrating one example of a fusion image displayed on the display unit according to the fourth embodiment. For example, as depicted in FIG. 15, the medical-image fluid-analysis-result fusion-image generation unit 146 can also superimpose a three-dimensional image of coronary arteries generated from volume data of a CT image and a three-dimensional analysis image based on three-dimensional data of a heart collected by an ultrasonic diagnostic apparatus on one another, and can display a fusion image in which a CT-FFR value is indicated on a coronary artery on the display unit 120. In this case, the alignment processing unit 145 aligns the volume data of the CT image with the volume data of the ultrasonic image. Based on this alignment information, the medical-image fluid-analysis-result fusion-image generation unit 146 then displays a fusion image in which the three-dimensional image of the coronary arteries, the three dimensional analysis image of the heart, and the fluid analysis result are combined.

Figure 16:
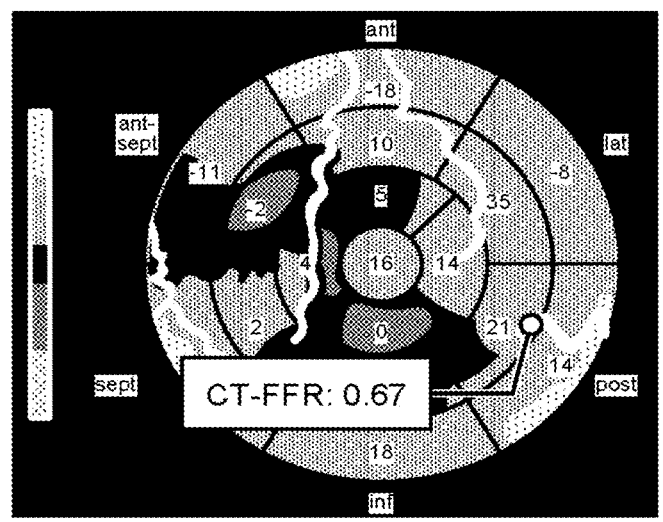
FIG. 16 is a diagram illustrating one example of a fusion image displayed on the display unit according to the fourth embodiment.

Furthermore, performing the above-described alignment also enables combination with other analysis images. FIG. 16 is a diagram illustrating one example of a fusion image displayed on the display unit according to the fourth embodiment. For example, as depicted in FIG. 16, the medical-image fluid-analysis-result fusion-image generation unit 146 can display, on the display unit 120, a fusion image in which a CT-FFR value is indicated at a blood vessel on a polar-map generated based on ultrasonic data. The polar-map herein is image data obtained by planarly expanding three-dimensional data in which three-dimensional cardiac-function information is mapped, and FIG. 16 is an image in which blood-vessel images indicating blood vessels are projected onto the polar-map.

In this manner, the medical-image processing apparatus 100 according to the present application displays a fusion image in which a fluid analysis result is indicated on a medical image, thereby making it possible to easily compare the fluid analysis result with the medical image. Herein, examples of the image on which the fluid analysis result is combined include a medical image used for generating an anatomical structure model used in the fluid analysis, an analysis image obtained by analyzing the medical image used for generating the anatomical structure model, a different type of medical image collected by a modality different from that for the medical image used for generating the anatomical structure model, or an analysis image obtained by analyzing the different type of medical image. Furthermore, the image on which the fluid analysis result is combined may be a single image out of the above-described images, or may be an image on which the medical image and the analysis image are combined.

In the above-described embodiments, cases have been described in which fluid analysis is performed by using a three-dimensional polygon model generated from a medical image. However, the embodiments are not limited to these cases, and may be cases in which the fluid analysis is performed by using volume data of the medical image. In this case, for example, the medical-image processing apparatus 100 extracts voxels corresponding to an inner wall of a coronary artery from the volume data of the medical image, and performs fluid analysis by using a group of the extracted voxels.

In the above-described embodiments, cases have been described in which the medical-image processing apparatus perform various processes. However, the embodiments are not limited to these cases, and may be used for medical-image diagnostic apparatus such as an ultrasonic diagnostic apparatus, a magnetic resonance imaging apparatus, and a nuclear-medicine imaging apparatus.

In the above-described embodiments, FFR is used as an example for an index relating to blood flow, but the embodiments are not limited to this, and CFR or other indices obtained by customizing these indices may be used.

In the above-described embodiment, coronary arteries have been considered, but the embodiments are not limited to this, and can be used for other blood vessels in the same manner.

The configurations of the medical-image processing apparatus described in the above-described embodiments are merely examples, and each configuration can be appropriately integrated or divided.

With the medical-image processing apparatus and the medical-image diagnostic apparatus according to at least one of the above-described embodiments, comparison between a fluid analysis result and a medical image can be easily performed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical-image processing apparatus, comprising:
    processing circuitry configured to
    acquire a first medical image containing a coronary artery and a second medical image containing a myocardial tissue,
    extract the coronary artery in the first medical image and the myocardial tissue in the second medical image;
    identify a positional relationship between the first medical image and the second medical image based on the extraction results of the coronary artery and the myocardial tissue,
    generate a blood flow image representing an index relating to blood flow that is analyzed through the coronary artery by fluid analysis on the first medical image, wherein the blood flow image represents the index relating to blood flow on the extracted coronary artery,
    generate a perfusion image showing a perfusion index representing a dynamic behavior of blood flow passing through the myocardial tissue, the perfusion index being obtained by perfusion analysis on the second medical image, wherein the perfusion image represents the perfusion index on the extracted myocardial tissue,
    generate a combined image by combining the blood flow image and the perfusion image based on the positional relationship,
    identify a dominant region on the myocardial tissue where a target branch of the coronary artery feeds blood,
    determine whether a myocardial abnormality is included in the dominant region based on the perfusion index,
    obtain the index relating to blood flow at the target branch of the coronary artery,
    calculate a treatment index indicating necessity of treatment for the target branch of the coronary artery using a determination result of the myocardial abnormality and the index relating to blood flow at the target branch of the coronary artery, and
    cause a display to display the treatment index in association with the target branch of the coronary artery on the combined image.

2. The medical-image processing apparatus according to claim 1, wherein the first medical image and the second medical image are collected respectively by different types of medical-image diagnostic apparatuses.

3. The medical-image processing apparatus according to claim 2, wherein the processing circuitry is further configured to
    analyze the index relating to blood flow in the coronary artery based on the fluid analysis using the first medical image, and
    analyze the perfusion index in the myocardial tissue based on the perfusion analysis using the second medical image.

4. The medical-image processing apparatus according to claim 1, wherein the processing circuitry is further configured to
    analyze the index relating to blood flow in the coronary artery based on the fluid analysis using the first medical image, and
    analyze the perfusion index in the myocardial tissue based on the perfusion analysis using the second medical image.

5. The medical-image processing apparatus according to claim 1, wherein the processing circuitry is further configured to
    extract information of each voxel position in the second medical image and store the information of each voxel position in a memory,
    identify a position of the index relating to blood flow and a position of the perfusion index in the second medical image based on the information of each voxel position, and
    perform a registration between a surface of the myocardial tissue and the index relating to blood flow based on the position of the index relating to blood flow and the position of the perfusion index in the second medical image.

6. The medical-image processing apparatus according to claim 1, wherein the processing circuitry is further configured to
    identify a position of the perfusion index in the second medical image,
    identify a position corresponding to a coronary artery region in the second medical image,
    identify a position of a 3D coronary model in the coronary artery region, the 3D coronary model being an anatomical structure model used to calculate the index relating to blood flow, and
    perform a registration between the perfusion index and the index relating to blood flow by identifying a relative position of the perfusion index, the coronary artery region and the 3D coronary model.

7. The medical-image processing apparatus according to claim 1, wherein the processing circuitry is further configured to
perform a registration between the blood flow image and the perfusion image, and
cause the display to display a fusion image in which the blood flow image and the perfusion image are superimposed based on a result of the registration.

8. An image processing method performed by a medical image processing apparatus, the image processing method comprising:
acquiring a first medical image containing a coronary artery and a second medical image containing a myocardial tissue;
extracting the coronary artery in the first medical image and the myocardial tissue in the second medical image;
identifying a positional relationship between the first medical image and the second medical image based on the extraction results of the coronary artery and the myocardial tissue;
generating a blood flow image representing an index relating to blood flow that is analyzed through the coronary artery by fluid analysis on the first medical image;
wherein the blood flow image represents the index relating to blood flow on the extracted coronary artery;
generating a perfusion image showing a perfusion index representing a dynamic behavior of blood flow passing through the myocardial tissue, the perfusion index being obtained by perfusion analysis on the second medical image, wherein the perfusion image represents the perfusion index on the extracted myocardial tissue;
generating a combined image by combining the blood flow image and the perfusion image based on the positional relationship;
identifying a dominant region on the myocardial tissue where a target branch of the coronary artery feeds blood, determining whether a myocardial abnormality is included in the dominant region based on the perfusion index,
obtaining the index relating to blood flow at the target branch of the coronary artery,
calculating a treatment index indicating necessity of treatment for the target branch of the coronary artery using a determination result of the myocardial abnormality and the index relating to blood flow at the target branch of the coronary artery, and
causing a display to display the treatment index in association with the target branch of the coronary artery on the combined image.

9. The image processing method according to claim 8, wherein the image processing method further comprising:
extracting information of each voxel position in the second medical image and store the information of each voxel position in a memory,
identifying a position of the index relating to blood flow and a position of the perfusion index in the second medical image based on the information of each voxel position, and
performing a registration between a surface of the myocardial tissue and the index relating to blood flow based on the position of the index relating to blood flow and the position of the perfusion index in the second medical image.

10. The image processing method according to claim 8, wherein the image processing method further comprising:
identifying a position of the perfusion index in the second medical image,
identifying a position corresponding to a coronary artery region in the second medical image,
identifying a position of a 3D coronary model in the coronary artery region, the 3D coronary model being an anatomical structure model used to calculate the index relating to blood flow, and
performing a registration between the perfusion index and the index relating to blood flow by identifying a relative position of the perfusion index, the coronary artery region and the 3D coronary model.

11. The image processing method according to claim 8, wherein the image processing method further comprising:
performing a registration between the blood flow image and the perfusion image, and
causing the display to display a fusion image in which the blood flow image and the perfusion image are superimposed based on a result of the registration.

12. A medical-image processing apparatus, comprising:
processing circuitry configured to
cause a display to display a combined image by combining a blood flow image representing indices relating to blood flow on a coronary artery and a perfusion image representing a perfusion index on myocardial tissue, wherein the indices relating to blood flow are analyzed through the coronary artery by fluid analysis on medical image data containing the coronary artery, the perfusion index represents a dynamic behavior of blood flow passing through the myocardial tissue and is obtained by perfusion analysis on medical image data containing the myocardial tissue,
obtain an index relating to blood flow at a target vessel of the coronary artery,
determine a correspondence between the target vessel and the perfusion index, the perfusion index being related to a myocardial abnormality,
calculate a treatment index indicating necessity of treatment for the target vessel of the coronary artery using the determined correspondence and the index relating to blood flow at the target vessel of the coronary artery, and
cause a display to display the treatment index in association with the target vessel of the coronary artery.

13. The medical-image processing apparatus according to claim 12, wherein the medical image data containing the coronary artery and the medical image data containing the myocardial tissue are collected respectively by different types of medical-image diagnostic apparatuses.

14. The medical-image processing apparatus according to claim 12, wherein the processing circuitry is further configured to
analyze the indices relating to blood flow in the coronary artery based on the fluid analysis using the medical image data containing the coronary artery, and
analyze the perfusion index in the myocardial tissue based on the perfusion analysis using the medical image data containing the myocardial tissue.

15. The medical-image processing apparatus according to claim 12, wherein the processing circuitry is further configured to
extract information of each voxel position in the medical image data and store the information of each voxel position in a memory, identify a position of the index relating to blood flow and a position of the perfusion index in the medical image data based on the information of each voxel position, and perform a registration between a surface of the myocardial tissue and the index relating to blood flow based on the position of the index relating to blood flow and the position of the perfusion index in the medical image data.

16. The medical-image processing apparatus according to claim 12, wherein the processing circuitry is further configured to identify a position of the perfusion index in the medical image data, identify a position corresponding to a coronary artery region in the medical image data, identify a position of a 3D coronary model in the coronary artery region, the 3D coronary model being an anatomical structure model used to calculate the index relating to blood flow, and perform a registration between the perfusion index and the index relating to blood flow by identifying a relative position of the perfusion index, the coronary artery region and the 3D coronary model.

17. The medical-image processing apparatus according to claim 12, wherein the processing circuitry is further configured to perform a registration between the blood flow image and the perfusion image, and cause the display to display a fusion image in which the blood flow image and the perfusion image are superimposed based on a result of the registration.

18. A medical-image processing method performed by a medical image processing apparatus, the image processing method comprising:

causing a display to display a combined image by combining a blood flow image representing indices relating to blood flow on a coronary artery and a perfusion image representing a perfusion index on a myocardial tissue, wherein the indices relating to blood flow are analyzed through the coronary artery by fluid analysis on medical image data containing the coronary artery, the perfusion index represents a dynamic behavior of blood flow passing through the myocardial tissue and is obtained by perfusion analysis on medical image data containing the myocardial tissue, obtaining an index relating to blood flow at a target vessel of the coronary artery, determining a correspondence between the target vessel and the perfusion index, the perfusion index being related to a myocardial abnormality, calculating a treatment index indicating necessity of treatment for the target vessel of the coronary artery using the determined correspondence and the index relating to blood flow at the target vessel of the coronary artery, and causing a display to display the treatment index in association with the target vessel of the coronary artery.

19. The medical-image processing method according to claim 18, wherein the medical image data containing the coronary artery and the medical image data containing the myocardial tissue are collected respectively by different types of medical-image diagnostic apparatuses.

20. The medical-image processing method according to claim 18, wherein the image processing method further comprising:

analyzing the indices relating to blood flow in the coronary artery based on the fluid analysis using the medical image data containing the coronary artery, and analyzing the perfusion index in the myocardial tissue based on the perfusion analysis using the medical image data containing the myocardial tissue.

21. The medical-image processing method according to claim 18, wherein the image processing method further comprising:

extracting information of each voxel position in the medical image data and store the information of each voxel position in a memory, identifying a position of the index relating to blood flow and a position of the perfusion index in the medical image data based on the information of each voxel position, and performing a registration between a surface of the myocardial tissue and the index relating to blood flow based on the position of the index relating to blood flow and the position of the perfusion index in the medical image data.

22. The medical-image processing method according to claim 18, wherein the image processing method further comprising:

identifying a position of the perfusion index in the medical image data, identifying a position corresponding to a coronary artery region in the medical image data, identifying a position of a 3D coronary model in the coronary artery region, the 3D coronary model being an anatomical structure model used to calculate the index relating to blood flow, and performing a registration between the perfusion index and the index relating to blood flow by identifying a relative position of the perfusion index, the coronary artery region and the 3D coronary model.

23. The medical-image processing method according to claim 18, wherein the image processing method further comprising:

performing a registration between the blood flow image and the perfusion image, and causing the display to display a fusion image in which the blood flow image and the perfusion image are superimposed based on a result of the registration.

24. A medical-image processing system, comprising:

processing circuitry configured to cause a display to display a combined image by combining a blood flow image representing indices relating to blood flow on a coronary artery and a perfusion image representing a perfusion index on a myocardial tissue, wherein the indices relating to blood flow are analyzed through the coronary artery by fluid analysis on medical image data containing the coronary artery, the perfusion index represents a dynamic behavior of blood flow passing through the myocardial tissue and is obtained by perfusion analysis on medical image data containing the myocardial tissue, obtain an index relating to blood flow at a target vessel of the coronary artery, determine a correspondence between the target vessel and the perfusion index, the perfusion index being related to a myocardial abnormality, calculate a treatment index indicating necessity of treatment for the target vessel of the coronary artery using the determined correspondence and the index relating to blood flow at the target vessel of the coronary artery, and cause a display to display the treatment index in association with the target vessel of the coronary artery.

25. The medical-image processing system according to claim 24, wherein the medical image data containing the coronary artery and the medical image data containing the myocardial tissue are collected respectively by different types of medical-image diagnostic apparatuses.

26. The medical-image processing system according to claim 24, wherein the processing circuitry is further configured to
analyze the indices relating to blood flow in the coronary artery based on the fluid analysis using the medical image data containing the coronary artery, and
analyze the perfusion index in the myocardial tissue based on the perfusion analysis using the medical image data containing the myocardial tissue.

27. The medical-image processing system according to claim 24, wherein the processing circuitry is further configured to
extract information of each voxel position in the medical image data and store the information of each voxel position in a memory,
identify a position of the index relating to blood flow and a position of the perfusion index in the medical image data based on the information of each voxel position, and
perform a registration between a surface of the myocardial tissue and the index relating to blood flow based on the position of the index relating to blood flow and the position of the perfusion index in the medical image data.

28. The medical-image processing system according to claim 24, wherein the processing circuitry is further configured to
identify a position of the perfusion index in the medical image data,
identify a position corresponding to a coronary artery region in the medical image data,
identify a position of a 3D coronary model in the coronary artery region, the 3D coronary model being an anatomical structure model used to calculate the index relating to blood flow, and
perform a registration between the perfusion index and the index relating to blood flow by identifying a relative position of the perfusion index, the coronary artery region and the 3D coronary model.

29. The medical-image processing system according to claim 24, wherein the processing circuitry is further configured to
perform a registration between the blood flow image and the perfusion image, and
cause the display to display a fusion image in which the blood flow image and the perfusion image are superimposed based on a result of the registration.

* * * * *